US011482315B2

(12) United States Patent
Song et al.

(10) Patent No.: US 11,482,315 B2
(45) Date of Patent: Oct. 25, 2022

(54) DEVICE ACCESSORY FOR DIGITALLY MONITORING AUTOINJECTOR USAGE FOR IMPROVED COMPLIANCE, REMOTE PATIENT MONITORING, AND ADHERENCE

(71) Applicant: MEDIMMUNE, LLC, Gaithersburg, MD (US)

(72) Inventors: Michael C. Song, Gaithersburg, MD (US); Janardhanan Anand Subramony, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 363 days.

(21) Appl. No.: 16/637,293

(22) PCT Filed: Aug. 9, 2018

(86) PCT No.: PCT/US2018/045932
§ 371 (c)(1),
(2) Date: Feb. 7, 2020

(87) PCT Pub. No.: WO2019/032784
PCT Pub. Date: Feb. 14, 2019

(65) Prior Publication Data
US 2021/0151160 A1 May 20, 2021

Related U.S. Application Data

(60) Provisional application No. 62/543,626, filed on Aug. 10, 2017.

(51) Int. Cl.
*G16H 20/00* (2018.01)
*G16H 20/17* (2018.01)
(Continued)

(52) U.S. Cl.
CPC ............ *G16H 20/17* (2018.01); *A61M 5/168* (2013.01); *A61M 5/16804* (2013.01);
(Continued)

(58) Field of Classification Search
CPC ........ G16H 20/17; G16H 40/67; G16H 10/60; A61M 5/168; A61M 5/16804; A61M 2205/3375
See application file for complete search history.

(56) References Cited

U.S. PATENT DOCUMENTS

2009/0069742 A1* 3/2009 Larsen .................... G16H 20/17
340/539.12
2010/0169111 A1* 7/2010 Brue ....................... G16H 40/67
340/541
(Continued)

FOREIGN PATENT DOCUMENTS

WO 2014/064691 A2 5/2014
WO 2016/118736 A1 7/2016

*Primary Examiner* — Tammara R Peyton

(57) ABSTRACT

A methodology to track patient usage of an autoinjector (AI) device, and to an external or electronic adaptor (eAdaptor) adapted to be used with the AI are disclosed. The eAdaptor contains sensors (including but not limited to a temperature sensor, a sound sensor, a vibration sensor and a magnetic sensor system), a display, a microprocessor, a real time clock, and communication systems that enables the eAdaptor to capture and confirm autoinjector (AI) use, as well as injection information, and transmit such information wirelessly to a smart phone or any other data receiving system or device. Also disclosed are an internal logic to operate the eAdaptor and a smart device APP that pairs with the internal logic to guide the patients with graphical user interface (GUI) displays on the smart device.

30 Claims, 32 Drawing Sheets

(51) Int. Cl.
*G16H 40/67* (2018.01)
*G16H 10/60* (2018.01)
*H04W 4/80* (2018.01)
*A61M 5/168* (2006.01)

(52) U.S. Cl.
CPC ............ *G16H 10/60* (2018.01); *G16H 40/67* (2018.01); *H04W 4/80* (2018.02); *A61M 2205/3375* (2013.01)

(56) References Cited

U.S. PATENT DOCUMENTS

| | | | |
|---|---|---|---|
| 2011/0060284 A1* | 3/2011 | Harr | A61M 5/14244 604/153 |
| 2013/0197445 A1 | 8/2013 | Schabbach et al. | |
| 2013/0310756 A1 | 11/2013 | Richard | |
| 2014/0207080 A1 | 7/2014 | Alderdings | |
| 2014/0330240 A1 | 11/2014 | Cabiri et al. | |
| 2015/0290396 A1 | 10/2015 | Nagar et al. | |
| 2016/0235915 A1 | 8/2016 | Cabiri et al. | |
| 2020/0254176 A1* | 8/2020 | Rytz | G16H 40/63 |

\* cited by examiner (a)  (b)  (c)

(a) (b)

(a)    (b)

Time in 0.03 sec increments

Figure 7
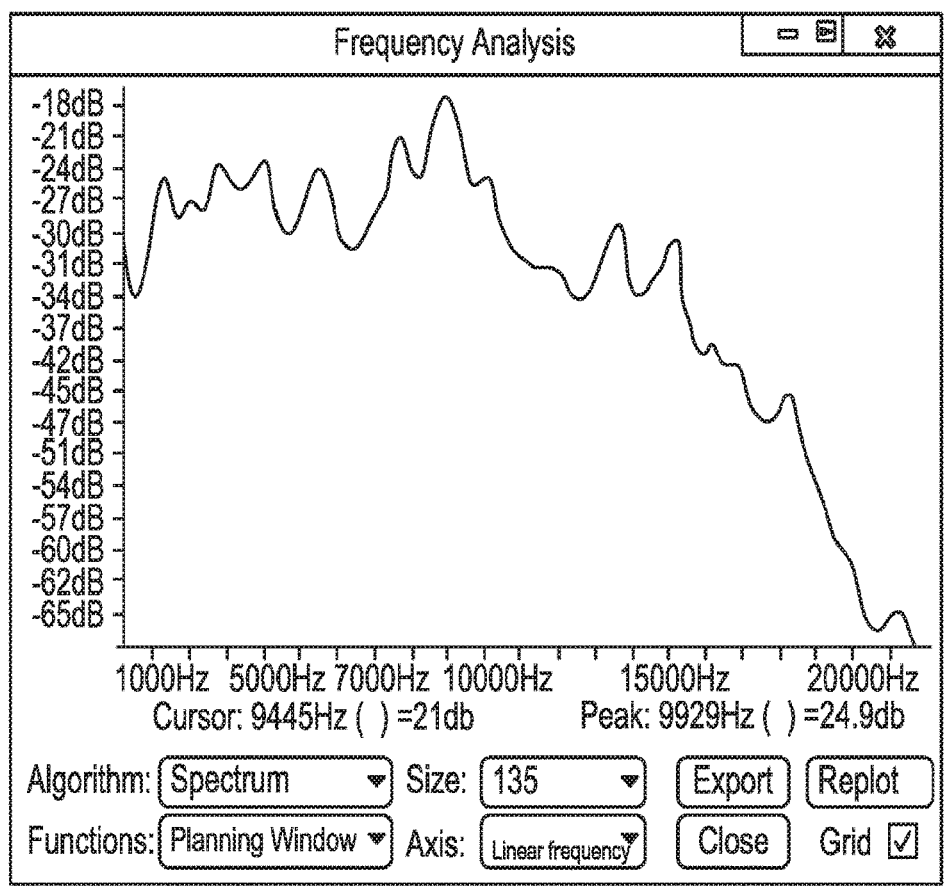
Start Sound Frequency domain
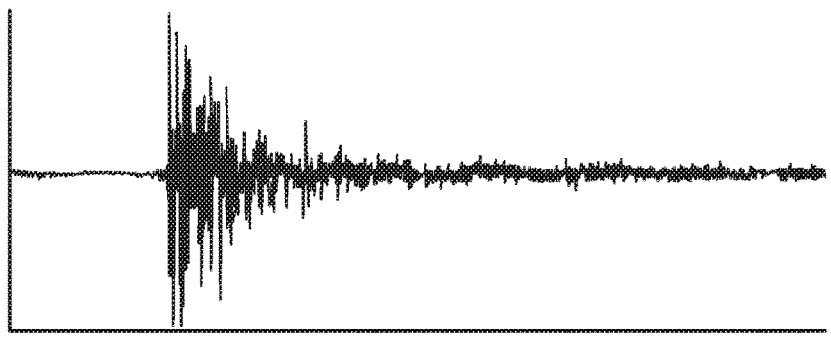
Start Sound Time domain

Figure 7 (cont)
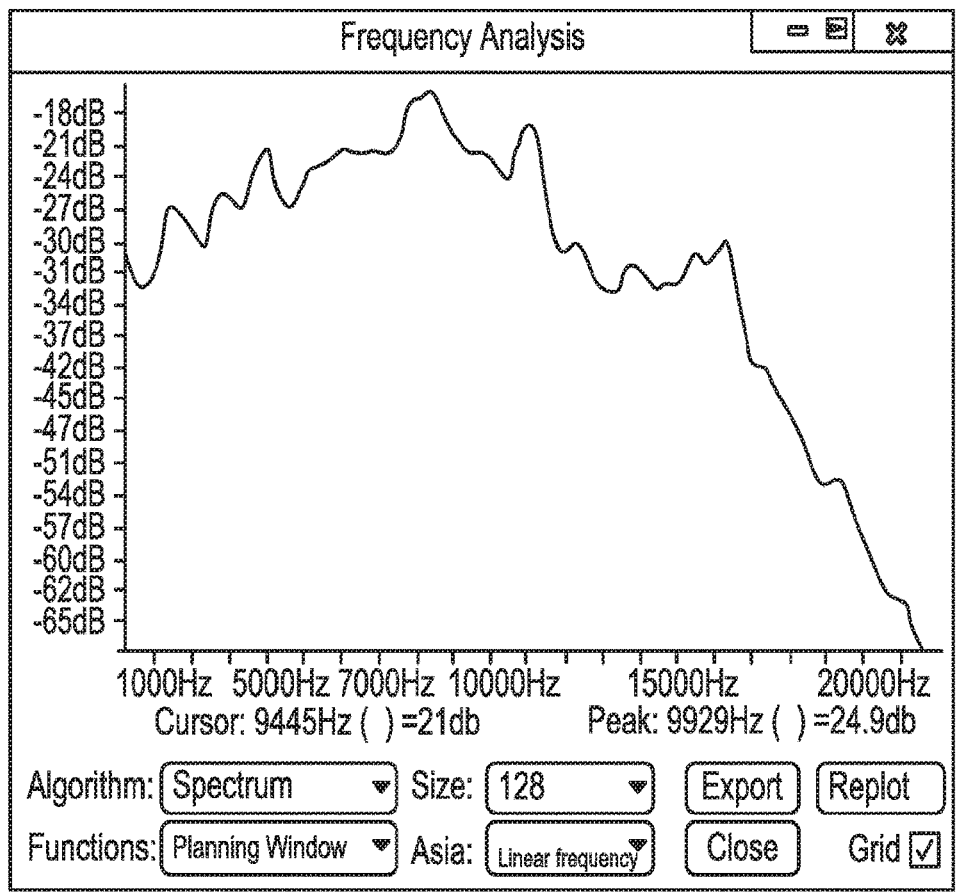
Stop Sound Frequency domain
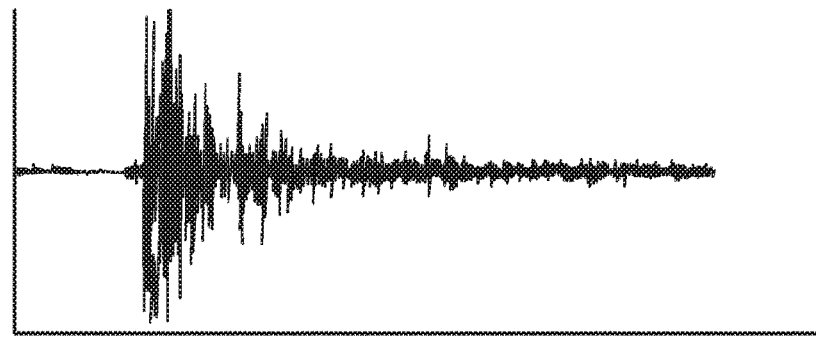
Stop Sound Time domain Figure 13
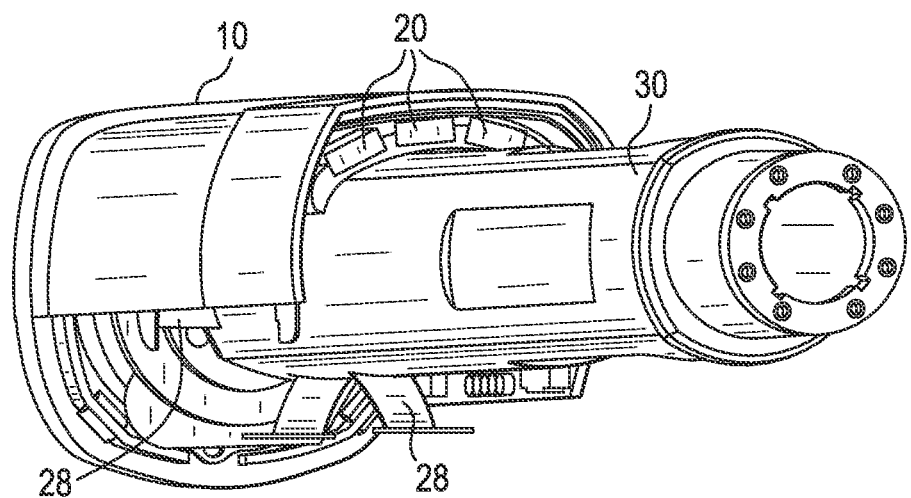
Figure 14
Figure 14a
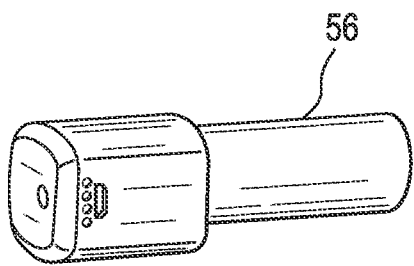
Figure 14b
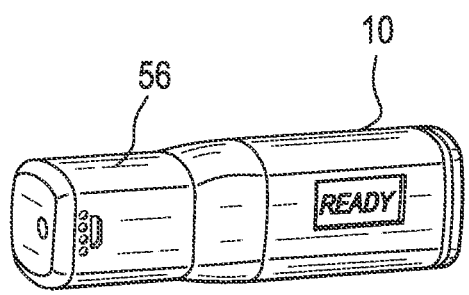
Power Pack at 0 degree

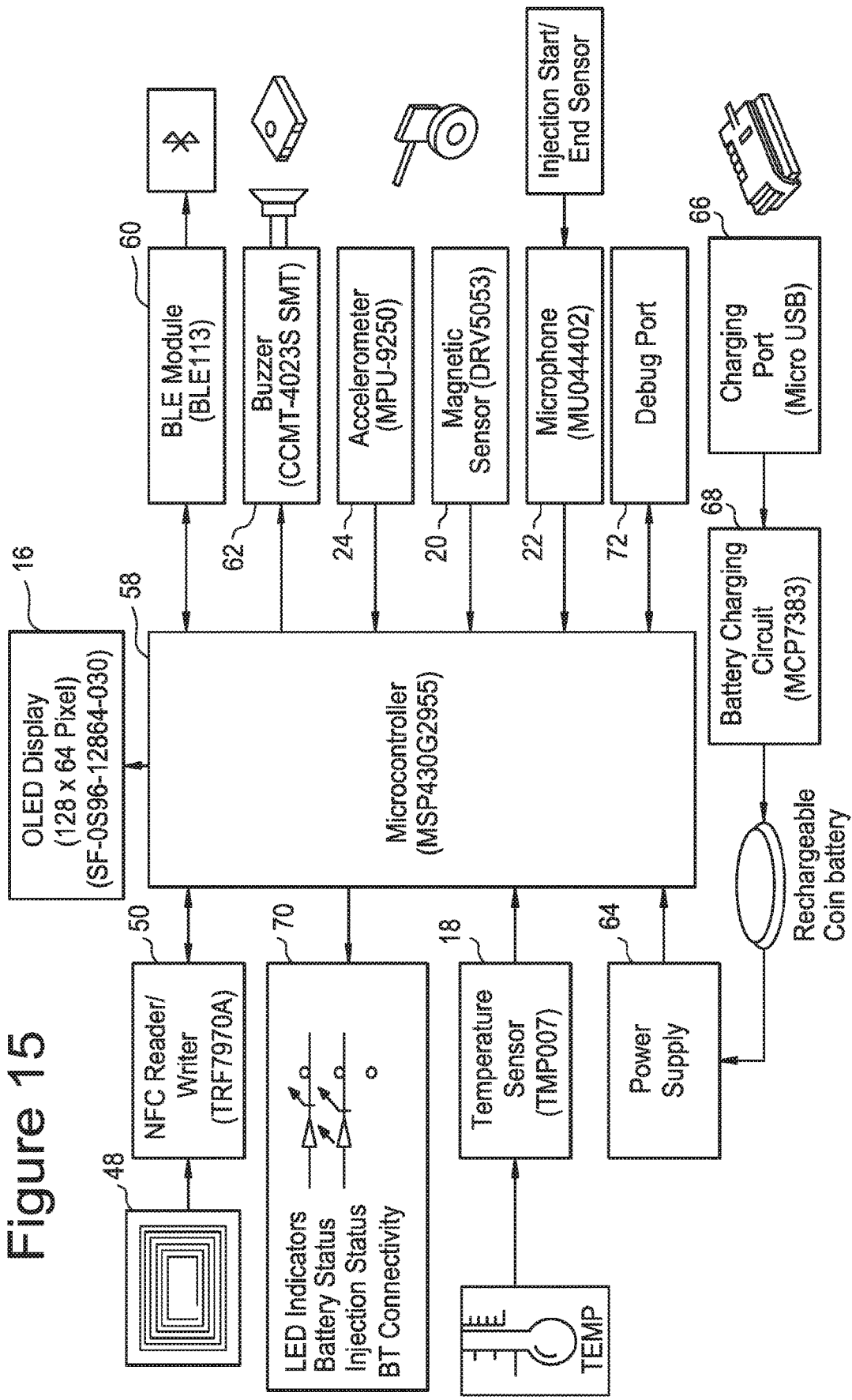

Figure 20
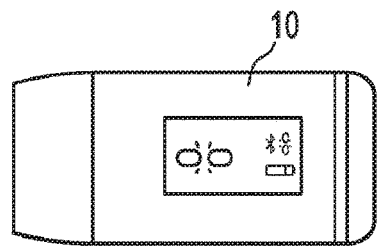
(a)
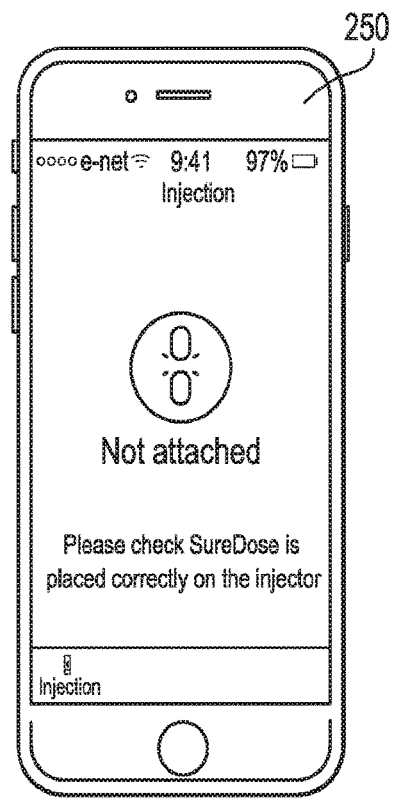
(b)
Figure 21
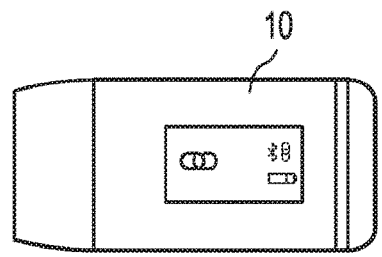
(a)
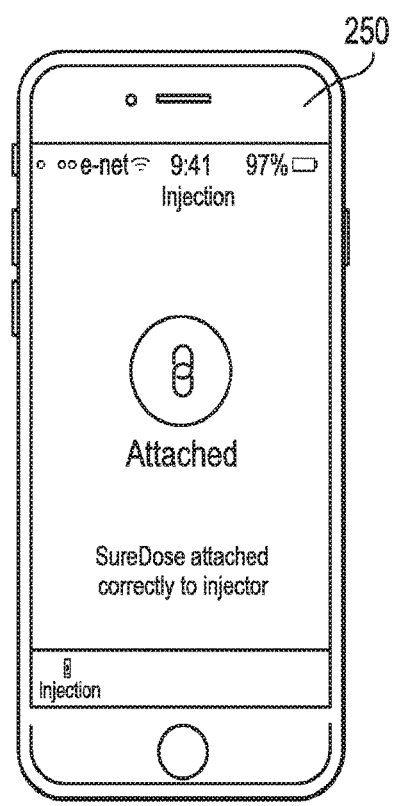
(b)

Figure 22
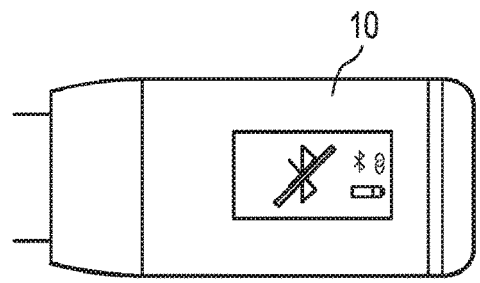
(a)
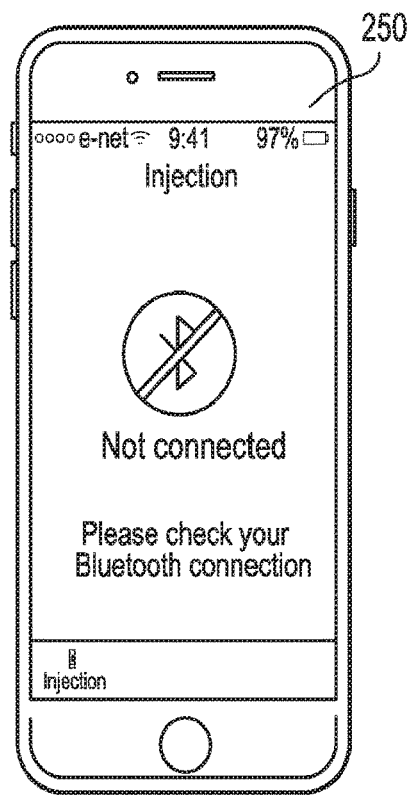
(b)
Figure 23
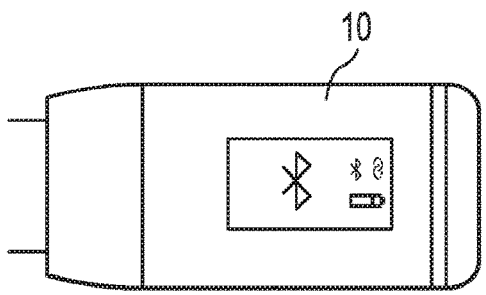
(a)
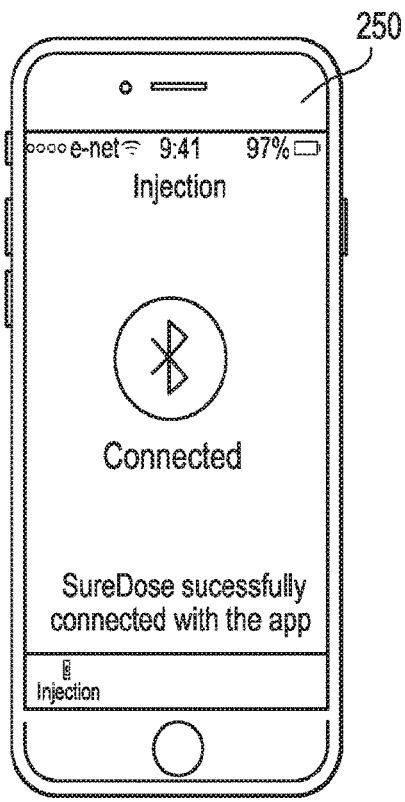
(b)

Figure 24
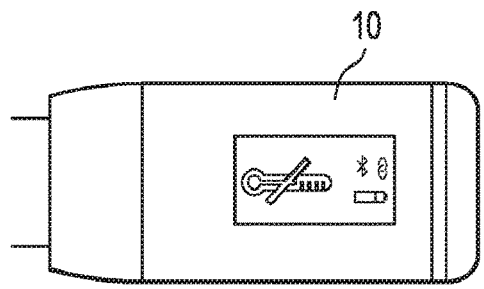
(a)
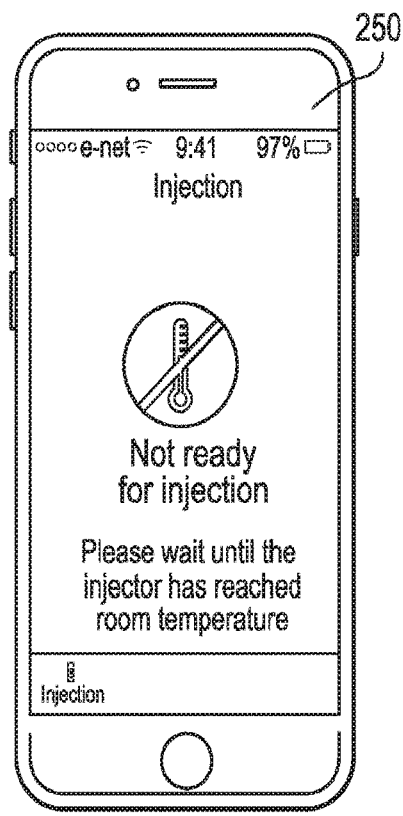
(b)
Figure 25
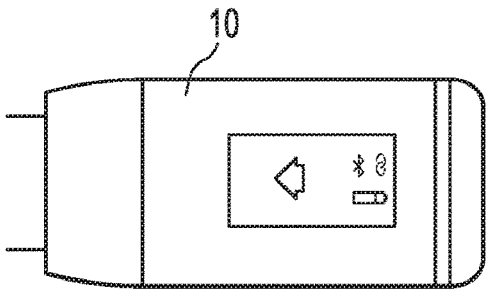
(a)
(b)

Figure 28
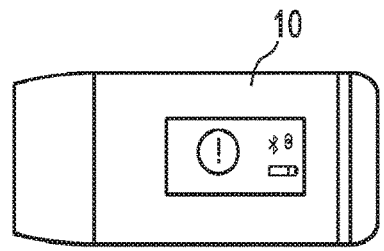
(a)
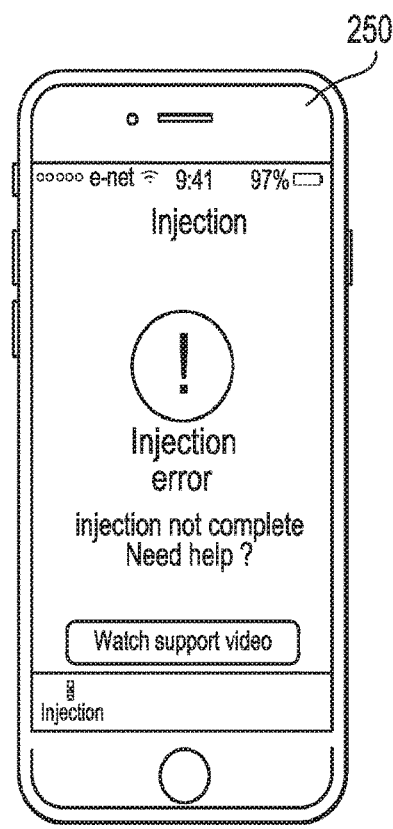
(b)
Figure 29
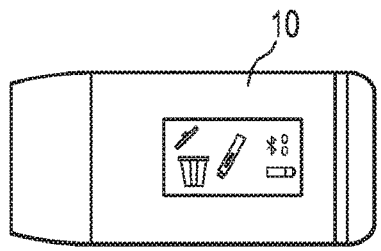
(a)
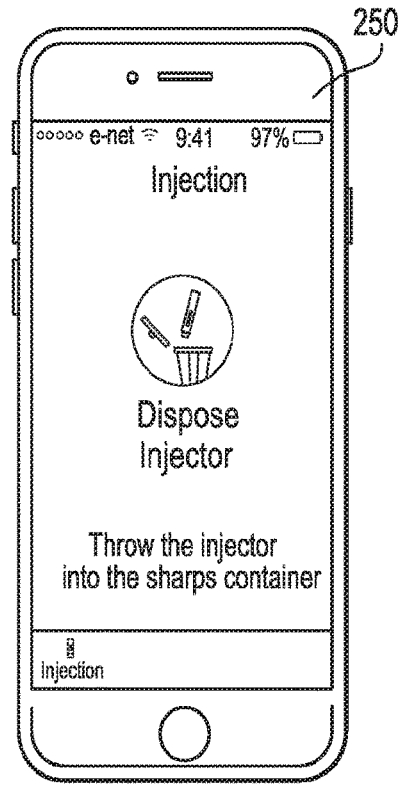
(b)

Figure 30
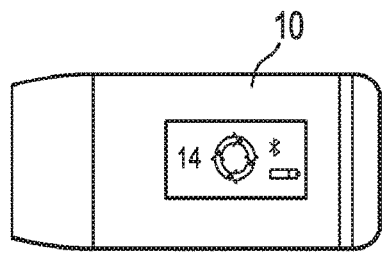
(a)
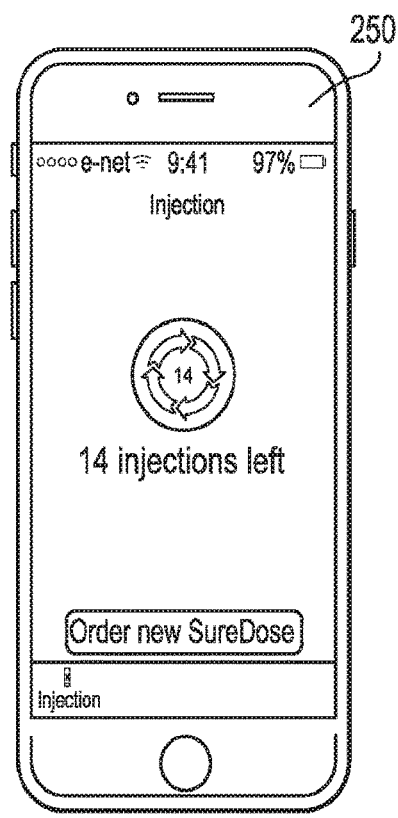
(b)
Figure 31
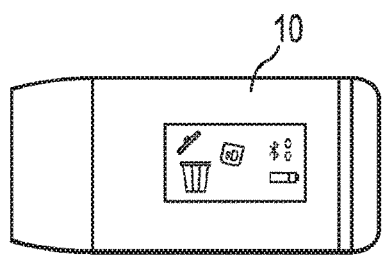
(a)
(b)

DEVICE ACCESSORY FOR DIGITALLY MONITORING AUTOINJECTOR USAGE FOR IMPROVED COMPLIANCE, REMOTE PATIENT MONITORING, AND ADHERENCE

FIELD OF THE INVENTION

The present invention generally relates to an external adaptor or electronic adaptor (eAdaptor) containing multiple sensors, a display, a microprocessor, a real time clock, and a communication system to track patient usage of a self injection device such as an autoinjector (AI) device and a methodology of operating the eAdaptor.

BACKGROUND OF THE INVENTION

Compliance of injection based therapies is known to be very poor. There have been studies that reported this growing problem. Only about fifty (50)% of the patients renew their prescriptions, and many drop out after initial weeks (see World Health Organization: "Adherence to Long-Term Therapies: Evidence for Action", January 2003, available at http://whqlibdoc.who.int/publications/2003/9241545992.pdf). To ensure optimal patient treatment it is essential for patients to comply with the medication regiments prescribed by their health care providers (HCPs). Similarly, because no two patients are identical, to ensure the best care and medication prescribed for the patients, the HCPs need to know that the patients are in compliance with their prescribed medication and have correctly and successfully self-administered their medication. This information will help HCPs and doctors to determine the efficacy of the medication. Correlating medication usage adherence with efficacy can lead to creation of precision therapy and in understanding what patient sub population would benefit from a given medicine. Similarly, knowing that the patients complied with their prescriptions and correctly self-administered (or administered with the help of HCPs) their medication is also important during clinical trials. Due to increased cost of health care, more and more of injections are now prescribed to be carried out by patients in a home setting versus done at the clinic by an HCP. Adherence for at home injection administration is therefore very important.

Conventional compliance tools utilize physical or digital journals, NFC labels, or Bluetooth connected AI cap add-ons to capture AI usage by patients. In addition, other prior art tools consist of electronic reminders to remind patients to take their medication. Both the physical or digital journal and NFC labels are dependent on patient truthfulness and compliance, and are only marginally effective. With such systems, a HCP will not be able to tell if, for example, a patient simply filled in their journals right before meeting the HCP to show compliance when the patient had not been compliant. With electronic reminders and NFC labels the patient may simply indicate injection to silence the alarms without actually self-medicating. Similarly, digitally connected AI caps have significant drawback in terms of tracking patient self-medication. The digital connected AI cap approach only provides confirmation that the patient have removed the AI cap but does not provide confirmation that the patient have self-medicated nor does it provide any information regarding when and whether the self-medication was successful.

As such, there exists a need for a methodology, an apparatus, and/or a device to capture injection information, such as but not limited to actual patient self-medication events, AI information (i.e. drug name), time when self-medication took place, the conditions of the AI injection device at time of injection, temperature of the formulation within the device (more about this in the next para), compliance with self-medication procedure, confirmation whether injection was successful or not, and to transmit such information wirelessly to a receiving smart device, such as a smart phone, to ensure patient compliance and allow the HCPs to determine the efficacy of the medication. Furthermore, there exists a need to account for the smart phone's limitation of communicating with only a single Bluetooth device at a time, or when smartphone connections are not available due to for example smartphone battery depletion or misplacement.

For biologics, the injection pain is related to the viscosity of the formulation within the AI. Since these devices are stored in the refrigerator, there is approximately a 20 min warm up time for the formulation to reach room temperature. Formulations at a colder temperature have higher viscosity and hence higher pain. Accurately monitoring the temperature of the formulation? along side compliance and device usage is a key criterion for successful combination product development and patient acceptability of the product. A discontinued product due to fear of injection pain (when injected cold) is loss of adherence and hence outcome.

SUMMARY OF THE INVENTION

The present invention generally relates to a methodology to track patient usage of an autoinjector device, and to an external, electronic adaptor or eAdaptor containing sensors (including but not limited to a temperature sensor, a sound sensor, a vibration sensor and a magnetic sensor system), a display, a microprocessor, a real time clock, and communication systems that enables the eAdaptor to capture and confirm autoinjector (AI) use, as well as injection information, and transmit such information wirelessly to a smart phone or any other data receiving system or device.

The present invention also includes a corresponding smartphone application (APP) that allows for features, such as auto and manual synchronization with the eAdaptor, two-way communication with the eAdaptor, visual display of AI and eAdaptor conditions, injection steps/counts, processing and conveyance of captured information, AI use and patient experience information; and retrieval and visualization of user use history. The stored usage data can be transferred to a back end system including external servers, secured internet cloud storage for remote patient monitoring by care givers, doctors, other HCPs or family members.

Furthermore the present invention also includes a smartphone APP that allows it to imitate or simulate any possible error combinations within a single eAdaptor use for training purposes.

The present invention is also directed an external adaptor adapted to receive an AI therewithin and to sense at least one characteristic of an injection by the AI at an injection site comprising:
  a sound sensor to detect a first sound produced by the AI at a start of the injection and a second sound produced by the AI at an end of the injection,
  a vibration sensor to detect a first movement produced by the AI at the start of the injection and a second movement produced by the AI at the end of the injection, and
  a real time clock (RTC) connected to a microprocessor to provide a timeline for the sensors, wherein the microprocessor determines a start time for the injection when the first sound detected by the sound sensor and the first movement detected by the vibration sensor substantially coincide on the time line and wherein the microprocessor determines an end time for the injection when the second sound detected by the sound sensor and the second movement detected by the vibration sensor substantially coincide on the time line.

The external adaptor may also comprise at least one magnetic sensor adapted to sense at least one magnetic member in the AI, wherein said at least one magnetic member is attached to a movable member in the AI and said movable member is moved from an initial location to a start location to start the injection, wherein at the initial location the at least one magnetic sensor senses a first magnetic reading, wherein at the start location the at least one magnetic member is proximate to the at least one magnetic sensor and the at least one magnetic sensor senses a second magnetic reading, which is higher than the first magnetic reading, and wherein the microprocessor determines a magnetic start time at the start location.

After the end of the injection, the AI is removed from the injection site, and the movable member returns at least to its initial location or beyond and the at least one magnetic sensor senses a third magnetic reading, which is less than or equal to the first magnetic reading, and wherein the microprocessor determines a magnetic removal time when the at least one magnetic sensor senses the third magnetic reading.

An injection duration is a difference between the start time and the end time. A total time at the injection site is a difference between the magnetic start time and the magnetic removal time. A hold time at the injection site is the total time at injection site less the injection duration.

The external adaptor may also have a temperature sensor, which can be an infrared temperature sensor or a thermistor. The external adaptor may also comprise a spring to bias the AI, a digital screen, at least one LED light and a speaker. The vibration sensor is preferably an accelerometer. The external adaptor may also have a near field communication (NFC) reader, which is adapted to read information on a NFC tag located on the AI.

The present invention is also directed a combination of an external adaptor and an AI, wherein the AI is received at least partially within the external adaptor, wherein the combination comprises:

at least one magnetic sensor disposed within the external adaptor and is adapted to sense at least one magnetic member in the AI, wherein said at least one magnetic member is attached to a movable member in the AI and said movable member is moved from an initial location to a start location to start an injection of the AI at an injection site, wherein at the initial location the at least one magnetic sensor senses a first magnetic reading, wherein at the start location the at least one magnetic member is proximate to the at least one magnetic sensor and the at least one magnetic sensor senses a second magnetic reading, which is higher than the first magnetic reading, and wherein a microprocessor using a real time clock (RTC) determines a magnetic start time at the start location.

After the end of the injection, the AI is removed from the injection site, and the movable member returns at least to its initial location or beyond and the at least one magnetic sensor senses a third magnetic reading, which is less than or equal to the first magnetic reading, and wherein the microprocessor determines a magnetic removal time when the at least one magnetic sensor senses the third magnetic reading.

The external adaptor of the combination may further comprise a sound sensor to detect a first sound produced by the AI at a start of the injection and a second sound produced by the AI at an end of the injection, a vibration sensor to detect a first movement produced by the AI at the start of the injection and a second movement produced by the AI at the end of the injection, and wherein the microprocessor determines a start time for the injection when the first sound detected by the sound sensor and the first movement detected by the vibration sensor substantially coincide on the time line and wherein the microprocessor determines an end time for the injection when the second sound detected by the sound sensor and the second movement detected by the vibration sensor substantially coincide on the time line.

The external adaptor and the AI may have substantially cylindrical shape and the AI is inserted into the external adaptor at any orientation. The at least one magnetic sensor comprises a predetermined effective sensing angular arc and a number of the at least one magnetic sensor and a number of the at least one magnetic member are determined based on said predetermined effective sensing angular arc. The at least one magnetic sensor comprises a plurality of magnetic sensors that are positioned to sense an angular arc of about 90°, and the at least one magnetic member comprises a plurality of magnetic members that are positioned about 90° apart. The external adaptor may have at least one spring to bias the AI toward the external adaptor.

The combination may also comprise a near field communication (NFC) reader located on the external adaptor, which is adapted to read information on a NFC tag located on the AI. Alternatively, the combination comprises a reader located on the external adaptor, which is adapted to read an identification code located on the AI, which can be a bar code or a matrix bar code connected to AI information stored on an external source, such as a computer storage or cloud storage.

The present invention is also directed to a method for operating an external adaptor adapted to receive an automatic injector (AI) therewithin and to sense at least one characteristic of an injection by the AI at an injection site comprising the steps of:

a. connecting the AI to the external adaptor,
b. determining when the AI reaches an injection temperature,
c. sensing for an injection start time,
d. sensing for an injection stop time,
e. sensing for a removal time from the injection site.

The injection start time is determined by a magnetic sensor system, a vibration sensor and/or a sound sensor. The injection start time can also be determined by a comparison between the vibration sensor and the sound sensor. The removal time is determined by the magnetic sensor. A hold time at the injection site after the injection is determined from the injection start time, the injection stop time and the removal time.

The method may also comprise the step of (f) reading an AI information from the AI and/or the step of (g) determining a failure mode. The failure mode exists when there is a failure to determine the injection start time, when there is a failure to determine the injection stop time, when there is a failure to determine the removal time from the injection site, when the AI has expired, when the external adaptor has expired or when the external adaptor has failed.

The inventive method may also comprise the step of (h) wirelessly connecting the external adaptor to a smart device. The present invention is also directed to an APP in a smart device adapted to pair with the method described above, wherein the smart device displays a graphical user interface (GUI) to a user. The APP may display a successful injection message to a user, at least one instruction after the successful injection message, which may include an instruction to hold the AI at the injection site for a predetermined time duration and/or an instruction to discard the AI. The APP may also display at least one failure mode, discussed above.

The present invention is also directed to a method for managing an idle time duration during an injection of an autoinjector (AI), comprising the steps of:
   a. connecting the AI to an external adaptor,
   b. monitoring a movement of the AI and external adaptor with an accelerometer,
   c. turning off a digital screen on the external adaptor if there is no movement after a first predetermined time period elapses, and
   d. if there is no movement after a second predetermined time period elapses, write to a memory that the AI has expired,
   wherein the second predetermined time period is longer than the first predetermined time period. The method may further comprise the step (e) of turning off the external adaptor if there is no movement after the second predetermined time period elapses.

BRIEF DESCRIPTION OF THE DRAWINGS

In the accompanying drawings, which form a part of the specification and are to be read in conjunction therewith and in which like reference numerals are used to indicate like parts in the various views:

FIG. 7 shows the start sound frequency and time domains and the stop sound frequency and time domains;

FIG. 13 is a bottom perspective, partial cutaway view of the eAdaptor, to show the AI being pushed by springs toward the eAdaptor's magnetic sensors;

FIG. 14. FIG. 14a shows a secondary component, such as a battery, that can be used with the eAdaptor; FIG. 14b shows this secondary component being attached to the eAdaptor;

FIG. 15 is a schematic diagram of the electronic components of the eAdaptor;

Figure 32:
Figure 33:
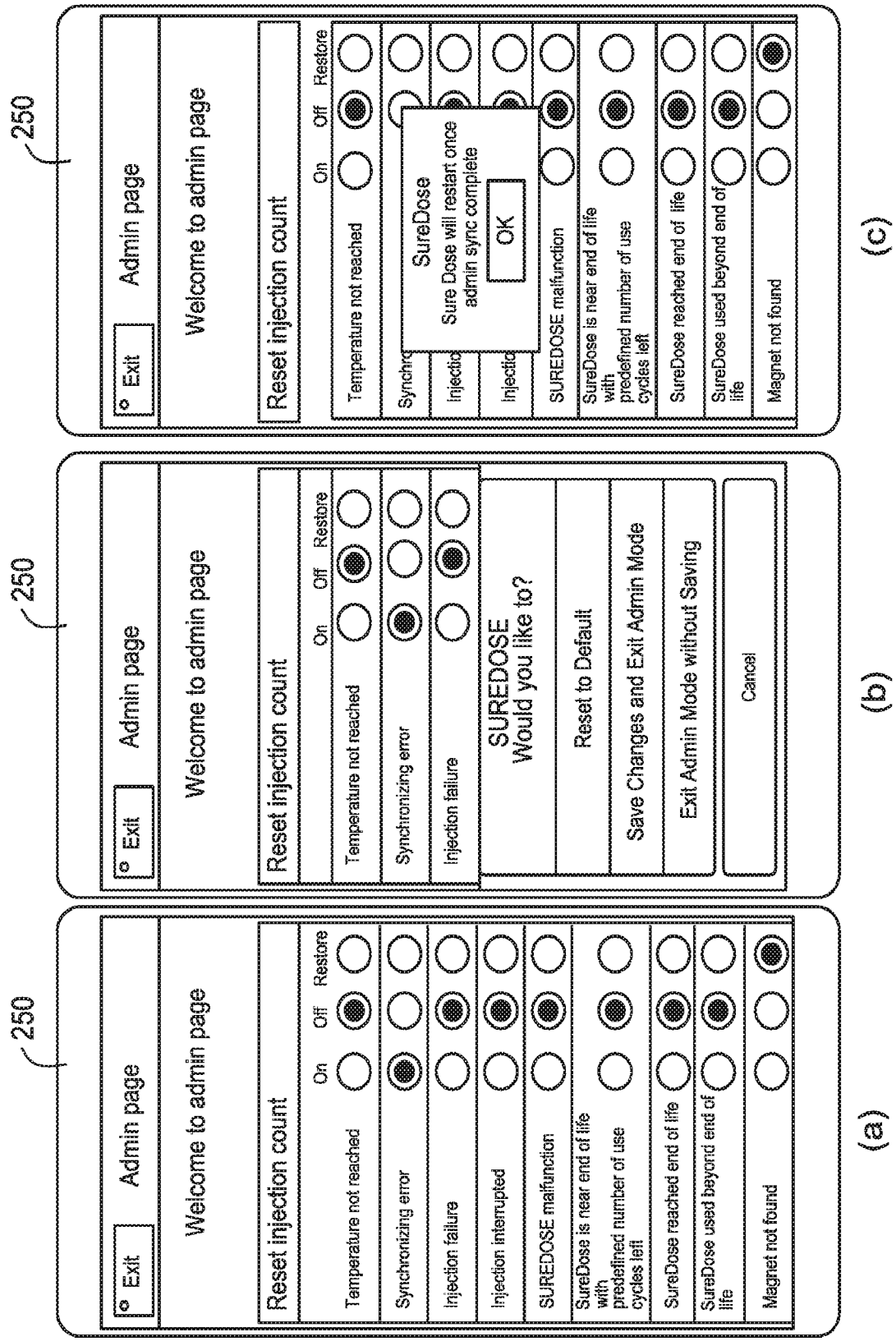

The subparts (a) of FIGS. 19-31 illustrate the various displays on the eAdaptor, and the subparts (b) (and (c) when used) of FIGS. 18-31 illustrate various GUIs displayed on the smart phone;

FIGS. 32a-32c show the injection results calculated from the injection data collected by the eAdaptor; and FIG. 33 illustrates GUIs displayed on the smart phone that allow a significant number of error scenarios for training and/or testing purposes.

DETAILED DESCRIPTION OF THE PREFERRED EMBODIMENTS

The present invention comprises a number of embodiments.

One embodiment of the present invention relates to technical advances within the attached-on or add-on reusable external, electronic adaptor or eAdaptor that interfaces with and captures AI usage information. The adaptor with embedded sensors effectively tracks the movement of the plunger rod that initiates the injection as well as captures at least two (2) other signals including sound and vibration.

Another embodiment of the present invention relates to an internal logic of the eAdaptor and a complementary APP for a smart device, which includes a smart phone or a smart tablet or another computing device with wireless connectivity, that captures the eAdaptor-transmitted information and provide feedback to user in conjunction with the eAdaptor display. The term "smart phone" when used individually or in combination with other computing device includes smart phone(s), smart tablet(s) and/or computing devices with wireless connectivity, such as WiFi, Bluetooth, NFC (near field communication), RF (radio frequency), and other known wireless connections.

Use of instructions for use (IFU) is a necessary aspect of correct usage of injection devices, such as AIs. However, often patients and caregivers don't follow the IFUs. One embodiment of this invention is the use of the APP and automatic start of the APP (without any additional step) once when the user opens the device for use. This instant pairing allows the apps and images to start on the smart phone which helps/guides the patients step by step for correct use.

Another embodiment of the present invention relates to another APP that trains HCPs and/or users on how to use the eAdaptor and can account for any situations with a single eAdaptor.

I. eAdaptor with Embedded Sensors and Connectivity

The complexity of the mechanical and inter-movable parts within conventional AIs presents challenges to integrating digital connectivity electronics and communication systems within the conventional AIs. Significant alteration of these AIs to enable full digital connectivity integration may jeopardize the AIs' functionality, robustness, size, and shape and sterility (if processed after medication filling/finishing). The inventive eAdaptor provides a system to capture the AIs' conditions using a modular approach and usage information without compromising or significantly alter AI components and designs. The inventive eAdaptor can also collect injection data from unaltered conventional AIs.

Another aspect of the eAdaptor is its reusability. Due to regulations that require recycling and disfavor disposable electronic components, it is desirable to develop a reusable electronic adaptor that can monitor several hundreds of injections. Particularly in countries with green policies, reusable adaptors are preferred over those that are not. The present invention addresses this aspect.

Figure 1:
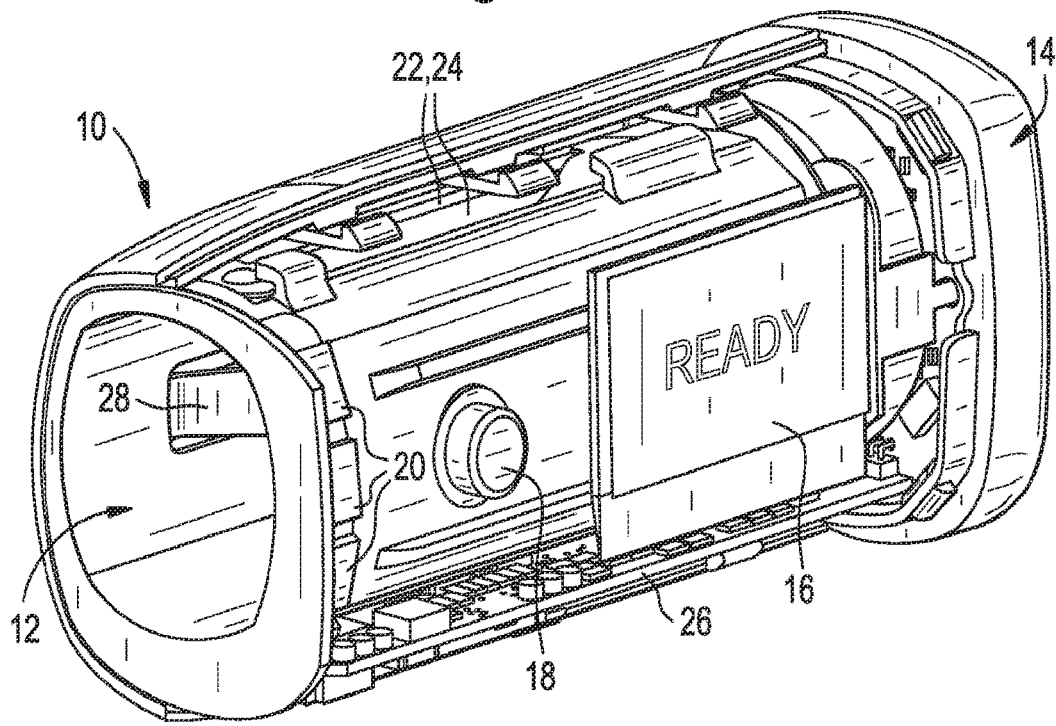
FIG. 1 is a right front perspective view of the inventive eAdaptor with a portion of the housing skin omitted to show internal features.

As best shown in FIG. 1, the inventive eAdaptor 10 is sized and dimensioned to work with a number of conventional AIs. eAdaptor 10 preferably has an open end 12 adapted to receive the AIs and a closed end 14. With a portion of the skin of the device omitted in FIG. 1, a number of electronic components within eAdaptor 10 are shown. Digital screen 16 is adapted to display information to HCPs or patients. Data is gathered by a number of sensors, such as temperature sensor 18, a plurality of magnetic sensors 20, sound sensor 22 and vibration sensor 24, which are described in details below. The electronics that control and operate eAdaptor 10 are positioned on printed circuit board 26. eAdaptor 10 may also contain one or more positioning devices, such as leaf spring 28, to help position the AIs within open end 12 to optimize data gathering.

Any conventional AI can be used with the inventive eAdaptor 10. The medication contained within the AIs needs to be refrigerated for preservation and is warmed to a proper injection temperature, e.g., room temperature, before injection. At lower temperatures the viscosity of the medication is typically higher and can cause painful injection. Suitable AIs may have certain electronic or connectivity components and may have built in sensors; however, as described below conventional AIs without such components can also be used with eAdaptor 10. AI 30, shown in FIGS. 2a-2c and other Figures, are described in conjunction with the inventive eAdaptor 10 to illustrate the present invention only. Suitable AIs include but are not limited to those manufactured by YpsoMed of Burgdorf, Switzerland such as the Ypsomate. The present invention is not limited to any particular AI, and the external form, form factor or foot print of the eAdaptor may change based on the type of AIs.

By way of example, and by no means limiting of the invention, the AI functions generally as follows: the autoinjector cap is removed the AutoInjector is ready to be fired; during the firing process, the safety shield/cover sleeve is depressed as the patient pushes the front end of the autoinjector against the injection site. The pushing up of the cover sleeve also cause the pushing up of a lock sleeve which activates the firing mechanism of the autoinjector resulting in the drug being expelled into the patient; after completion of injection, the user lifts up the autoinjector off the site of injection which causes the lock sleeve to be extended back down and into a lock mode (preventing the cover sleeve from being able to be pushed back up again). During the activation and finish of injection, the autoinjector produces an audible mechanically induced click sound which also creates a vibrational signal; as is further described below, this functionality can be used with embodiments of the present invention.

Figure 2:
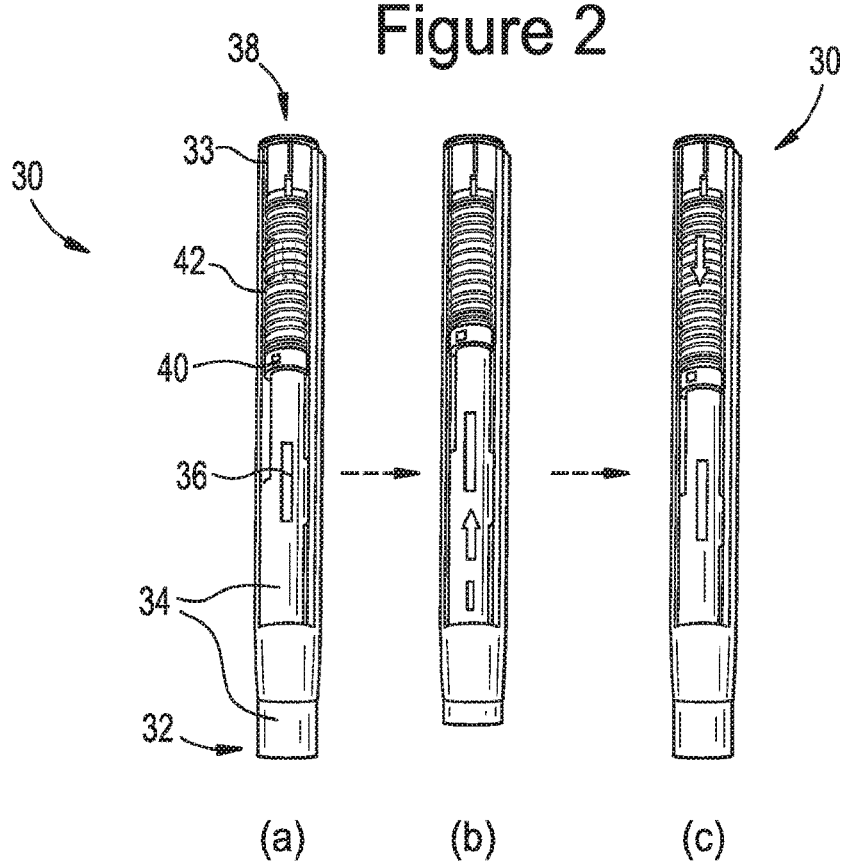
FIGS. 2a-2c are front views of an automatic injector (AI) with a portion of the housing skin omitted to show internal features and show a sequence of injection steps.

Generally, AI 30 has an injection end 32 and back end 33, where front shield 34 hides a needle that projects out of injection end 32 to inject a medication contained in syringe 36. Front shield 34 abuts a power unit 38 that comprises a lock sleeve 40 movable toward back end 33 to compress spring 42, and a piston that moves toward injection end 32 to eject the medication. AI 30 typically has a removable cover (not shown) attached to front shield 34 at injection end 32 to prevent debris from entering the AI and to protect the needle. AI 30 shown in FIG. 2a is in the pre-injection configuration. To inject the medication AI 30 is brought to the injection site, e.g., the patients' skin, and AI 30 is pressed against the patients' skin, as illustrated in FIG. 2b. This action caused front shield 34 to move upward, as shown by the arrow, compressing spring 42 and pushing lock sleeve 40 upward until the piston is triggered and pushes the medication out of syringe 36 into the patients. The configuration shown in FIG. 2b, which shows a maximum height that lock sleeve 40 travels, is maintained until AI 30 is removed from the injection site, as shown in FIG. 2c, and lock sleeve 40 moves away from back end 33 as shown by the arrow in FIG. 2b. In one embodiment, lock sleeve 40 may move past its initial position shown in FIG. 2a to be permanently locked in place preventing a reuse of the AI.

AI 30 is designed to produce a first sound at the beginning of the injection when lock sleeve 40 reaches its maximum upward travel and a second sound when the piston completes its downward movement to push the medication out of syringe 36. Generally, the IFU for the AIs would instruct the patients or HCPs to hold the AIs at the injection site for a predetermine time period after the injection is completed, i.e., shown in FIG. 2b, to prevent premature removal of the AIs or wet injections.

According to the present invention, these characteristics of the AIs are measured or sensed by the inventive eAdaptor 10, and AI 30 is preferably embedded with sensors and/or relevant information about the AI that can be transmitted to the eAdaptor upon connection. eAdaptor 10 is designed to be wirelessly connected, preferably by Bluetooth, to a smart device, such as a smart phone.

Figure 3:
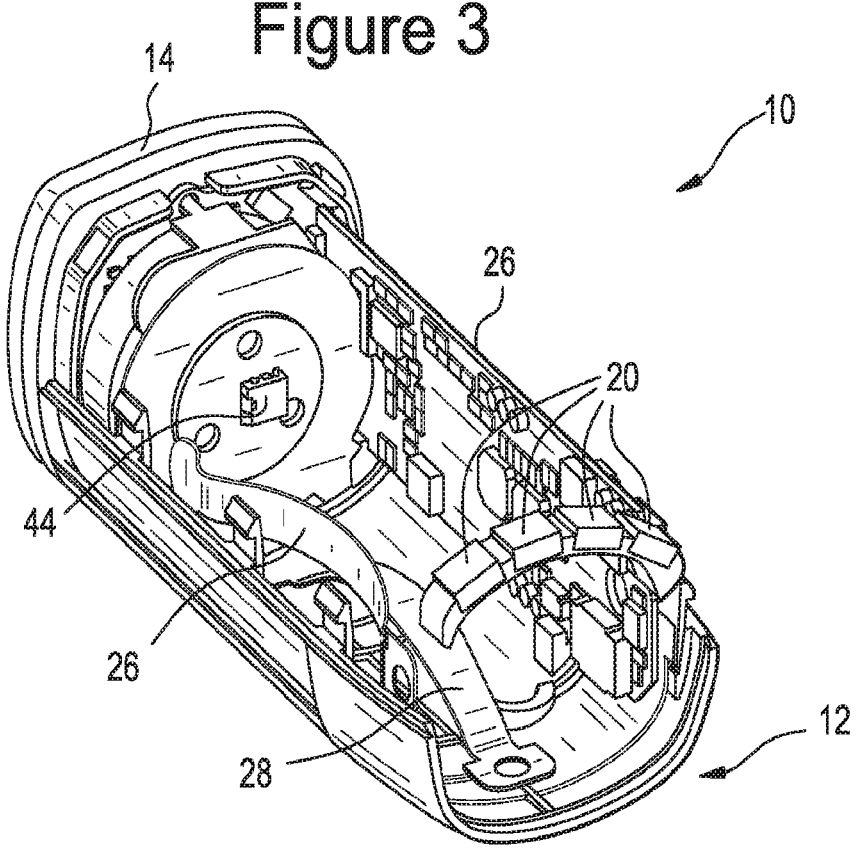
FIG. 3 is a left front perspective view of the inventive eAdaptor with certain features omitted for clarity.

Conventional smart phone typically has only one Bluetooth communication port that can only be paired with one compatible Bluetooth device. Hence, to connect to eAdaptor 10, the smart phone must be disconnected to other Bluetooth-enabled devices. In order to minimize the time period that eAdaptor 10 occupies the smart phone, eAdaptor 10 is provided with switch 44, as shown in FIG. 3. Switch 44 is located at the end of open end 12 and is activated when an AI is fully inserted into eAdaptor 10. Switch 44 can be an electrical-mechanical contact switch, e.g., a pogo switch, and contact with the back end 33 of AI 30 turns eAdaptor 10 on. Switch 44 may also be a proximity or optical switch that turns eAdaptor 10 on when the back end 33 is brought into close proximity with the switch. Once turned on, eAdaptor 10 would pair with a smart phone that contains the necessary software/APP to assist the patients and HCPs with the injection and to collect injection data, as discussed below.

Alternatively, eAdaptor 10 has a separate ON/OFF switch and switch 44 is used to turn the Bluetooth functionality on or off as described above.

eAdaptor may also automatically turns itself off after the injection and hold time per the IFU are completed and the injection data is either stored or transmitted to the smart phone, or wait a predetermined amount of time before doing so. The internal logic of eAdaptor 10 may also wait for a confirmation signal from the smart phone before turning off or entering auto-sleep mode to turn off Bluetooth connectivity.

Relevant AI information include, but are not limited to, drug name, lot number, expiration date and other essential information that will help ensure that the patients inject the correct medication, as prescribed by the HCPs. Furthermore, capturing this information provides additional assurances to the patients and underscores safety, i.e., the right drug for the right patient. This is an improvement over reliance on the patients to self-check expiration date and proper medication. eAdaptor 10 can read this information and automatically conduct checks and notify patients and/or HCPs if the medication had expired, and can reject expired AIs.

Such relevant AI information can be stored on a near field communication (NFC) tag or label 48 applied or attached to AI 30 during manufacturing. NFC tag 48 can be read by a NFC reader 50 stored on the eAdaptor, as shown in FIGS. 4a-4b, using electromagnetic induction. NFC tag 48 carries the AI information that NFC reader 50 can read at close range. Communication between tag 48 and reader 50 can occur at distances of less than 20 cm and normally at distances of less than 4 cm (1.6 inch). The NFC tag 48 can be encoded and information can be written on tag 48 at any point before AI 30 is used. Since NFC reader 50 is positioned deep inside eAdaptor 10, the probability of the NFC reader reading unintended NFC tags is minimized. Preferably, additional information cannot be written to NFC tag 48 after the AI information is written thereon to ensure that the AI information is not erased. Alternatively, a portion of the NFC tag is available to accept additional information, such as additional data that the AI had been deployed and the patients should not try to reuse a spent AI. Such additional information can be written on tag 48 by reader 50. To shield NFC reader from reading unintended information, a shield 52 may be positioned on the back side of reader 50 away from the side that would be reading tag 48. Shield 52 can be made from a ferrite material. Alternatively, tag 48 can be positioned inside AI 30, but sufficiently close to the outer housing of AI 30 to be read by reader 50. NFC tags and readers are discussed in U.S. Pat. No. 9,037,083 and U.S. published patent application No. US 2015/0106113, which are incorporated by reference herein their entireties.

Alternatively, relevant AI information can be stored on a website or internet cloud storage and the AI is provided with an identification code, such as bar code, 2D bar code or QR tags or matrix barcode. The smart phone may scan this identification code, which uniquely identifies the AI and the internet address/website where the relevant AI information is located and can be downloaded to the smart phone. This information can be transmitted via Bluetooth to eAdaptor 10. Optionally, eAdaptor 10 may have an optical sensor to scan the identification code and either transmits this code to the smart phone to obtain the information from the internet or to directly obtain such information.

To ensure that the information captured is correctly associated with the date and time, the electronics on PCB 26 preferably comprises an internal real time clock (RTC). Any RTC chip can be selected and included on PCB 26. Suitable RTC chips include, but are not limited to, DS1302, DS1307, etc. To ensure consistent and accurate time and date information, each time eAdaptor 10 is connected to the smart phone, the time and date of the RTC on PCB 26 are synchronized with those on the smart phone. Preferably, the time zone information on the smart phone is also synchronized or written to the RTC.

The IFU recommends that after the AIs are removed from refrigeration, and the patients and/or HCPs should wait a sufficient time, e.g., about 20 minutes or 15 or 10 minutes depending on the particular AIs, for the AIs to reach room temperature for injection. Cold injections or injections at temperature lower than room temperature can be painful to the patients due to higher viscosity of the medication at lower temperatures.

As shown above in FIG. 1, eAdaptor 10 includes temperature sensor 18. Temperature sensor 18 can be an infrared temperature sensor, a thermistor, a thermocouple or any known thermometer that can be read by the internal electronics. An infrared thermometer is a thermometer which infers temperature from thermal radiation, known as blackbody radiation, emitted by the object being measured, i.e., AI 30. Infrared temperature sensor is advantageous because it can read temperature without being in physical contact with AI 30. As illustrated in FIG. 1, temperature sensor 18, which is preferably an infrared sensor or a direct contact thermistor, is pointed toward the open cavity in eAdaptor 10, which would receive AI 30, to obtain a temperature of the AI. Since the medication syringe 36 is internal to AI 30, the medication's temperature is expected to be different than the AI's sensed temperature, due to the fact that it takes longer for heat from the atmosphere to flow into the center of the AI where the medication syringe is located. Hence after insertion of the AI into the eAdaptor, the outer surface of the AI would reach room temperature before the internal syringe. Hence, there is a temperature offset between the internal syringe and the exterior of the AI. This temperature offset can be determined by experimentation and calibration, since this temperature offset is determined by the geometries of various AIs, the room temperature and the coefficient of thermal conductivity of the medication and of the AIs. In one embodiment, when the exterior of the AI reaches room temperature as measured by temperature sensor 18, eAdaptor 10 would count until a calibrated time is reached to ensure that the internal medication temperature also reaches room temperature. Preferably, eAdaptor 10 continuously monitors the temperature of AI 30 or at predetermined time increments, e.g., 0.1 second or 1 second. eAdaptor 10 records the time and date when AI 30 and the medication reach room temperature using the RTC.

Alternatively, NFC tag 48 also contains the necessary wait time as a function of room temperature and after NFC reader 50 obtains such information eAdaptor 10's internal logic can count down the necessary wait time for the medication to reach room temperature before informing the patients and/or HCPs via screen 16 or the smart phone's screen that it is optimal time to inject the medication.

Figure 4:
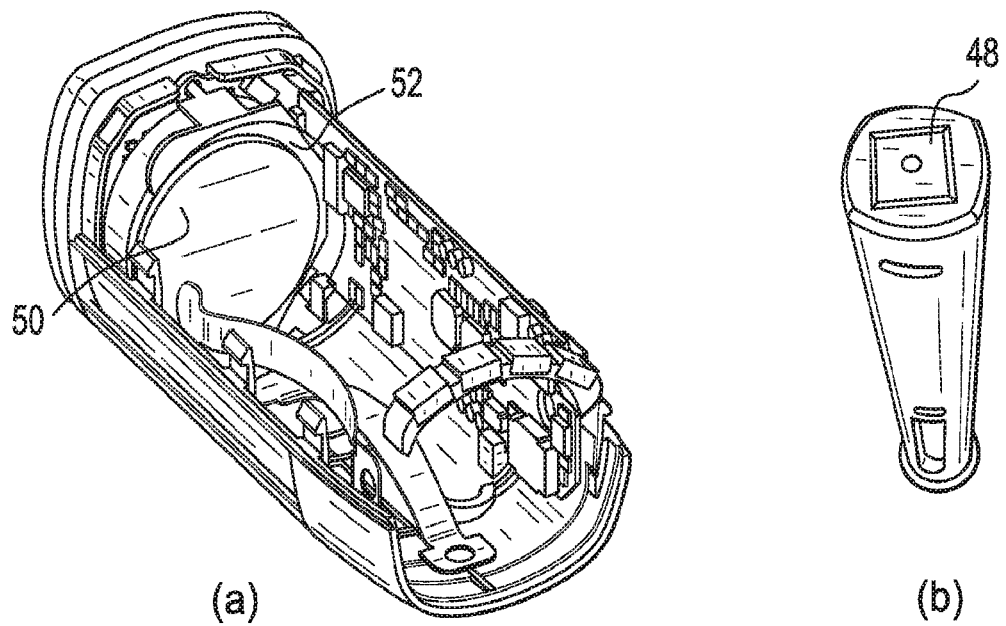
FIG. 4a shows the eAdaptor of FIG. 3 with additional features omitted.
FIG. 4b is an end perspective view of an AI with a NFC tag.

The inventive eAdaptor also uses magnetic proximity sensors to sense usage information for the AI. More specifically, eAdaptor 10 deploys one or more magnetic sensors 20 as shown in FIGS. 1, 3 and 4. These sensors can be Hall-effect type sensors. Magnetic force/field readings from these magnetic sensors can be read by the electronics on PCB 26. Complementary magnetic members 54, preferably permanent magnets or ferrous materials that can affect the magnetic fields generated by magnetic sensors 20, are preferably positioned on an internal moving member within AI

Figure 5:
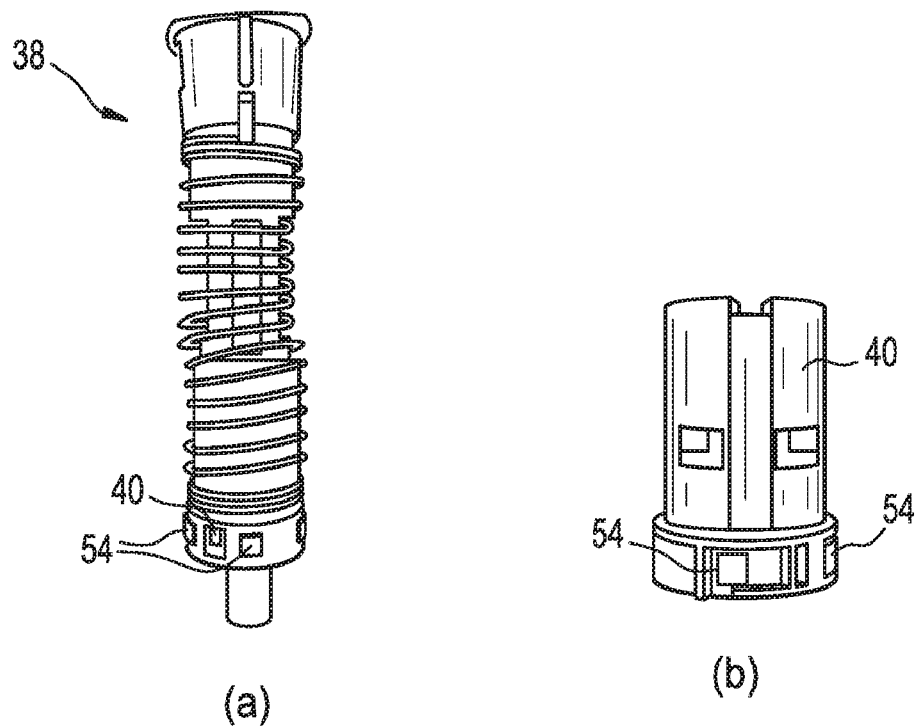
FIG. 5a is a front view of an AI power unit with magnetic members attached to a lock sleeve.
FIG. 5b is a front view of the lock sleeve.

30. Preferably, magnetic members 54 are located on the movable lock sleeve 40 of AI power unit 38, as shown in FIGS. 5a-5b. As discussed above in connection with FIGS. 2a-2c, at the start of the injection lock sleeve 40 moves upward and is held at that maximum height until the patients remove the AI from the injection site and then lock sleeve 40 moves downward to the lock position.

Figure 6:
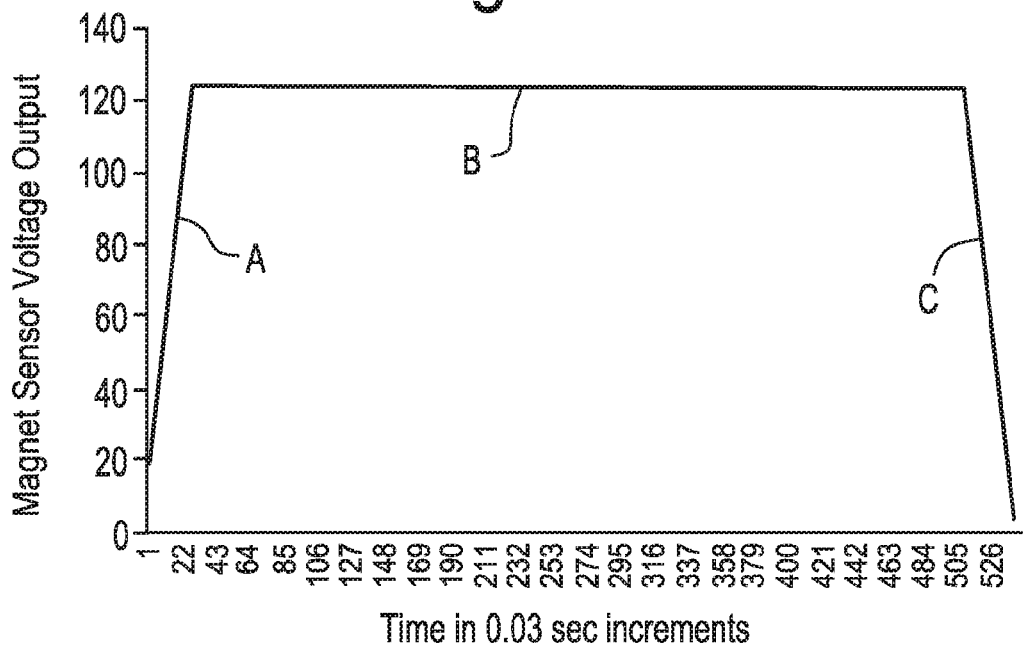
FIG. 6 is a graph showing the strength of the magnetic sensor(s) during an injection.

Preferably, at this maximum height magnetic members 54 on AI 30 and magnetic sensors 20 on eAdaptor 10 are proximate to each other to optimize the magnetic field therebetween. As shown in FIGS. 5a-5b and FIGS. 1, 3 and 4, magnetic members 54 are located at or near the bottom of lock sleeve 40 and magnetic sensors 20 are located at or near open end 12 of eAdaptor 10, so that the magnetic sensors 20 and magnetic members 54 are proximate to each other at the beginning of the injection to optimize the magnetic fields. Referring to FIG. 6, a representative graph of the strength of the magnetic field (in voltage output) as a function of time is shown. First segment A represents the upward travel of magnetic members 54 located on lock sleeve 40 toward magnetic sensors 20 from FIG. 2a to FIG. 2b. The time period that includes the injection of medication from AI 30 into the patient and the hold time after the injection is represented by second segment B, where lock sleeve 40 remains substantially stationary. Segment C represents the travel of lock sleeve 40 downward passed its initial position to its locked position. The segment B measured in time (horizontal axis) is the combination of injection time and hold time.

Figure 8:
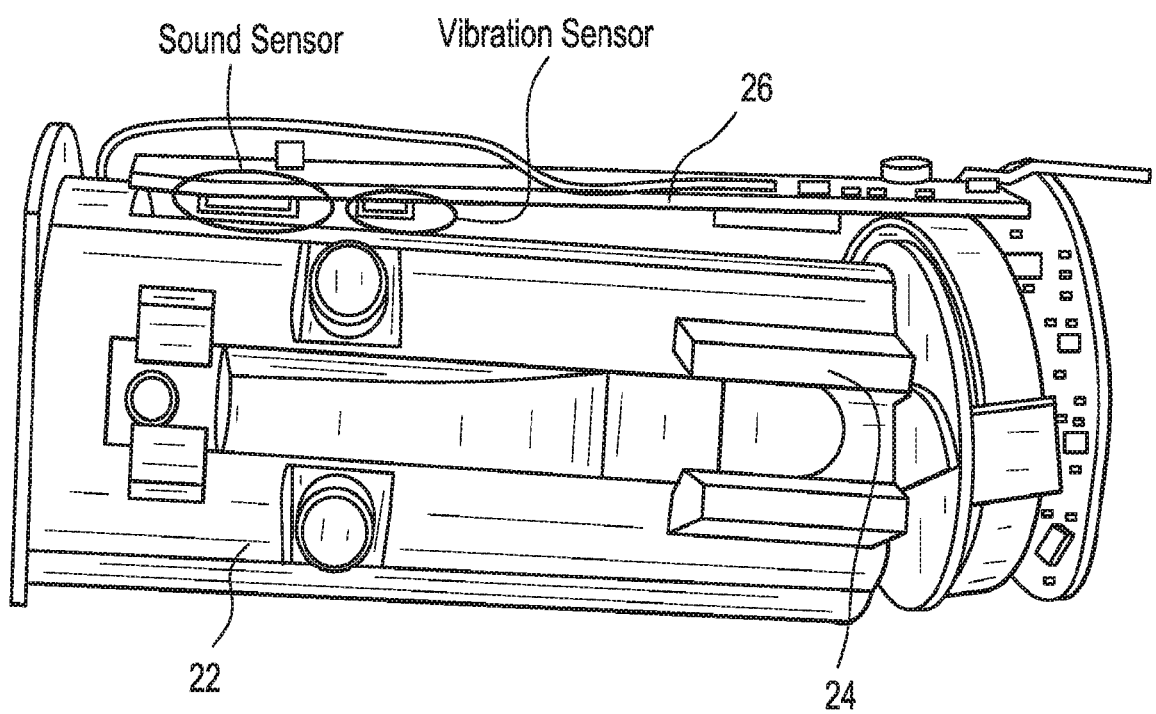
FIG. 8 is a front view of the eAdaptor with a portion of the housing skin remove to show the vibration and sound sensors.
Figure 9:
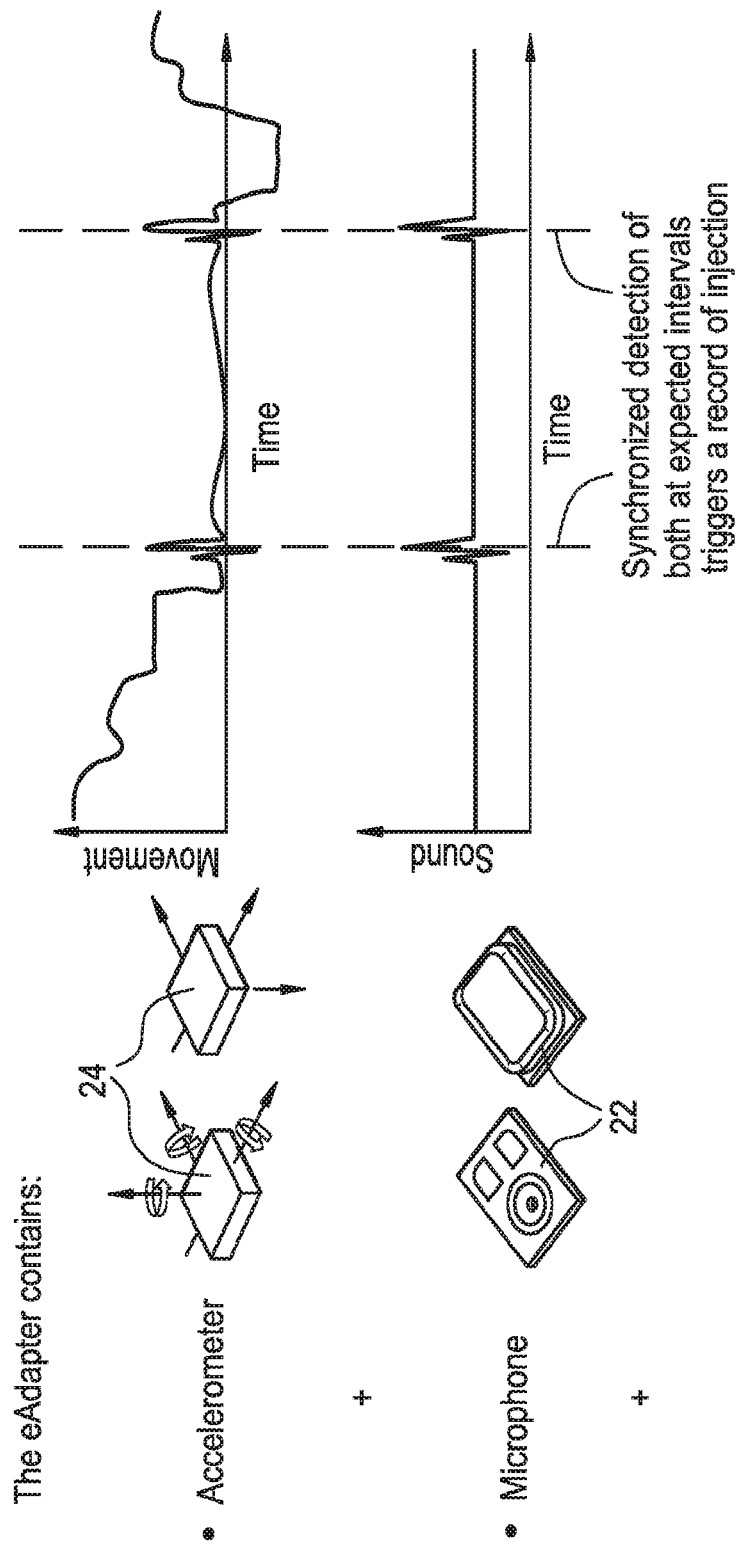
FIG. 9 shows the injection start and stop spikes sensed by the vibration and sound sensors.

As discussed above, AI 30 produces a sound at the start of the injection and another sound at the end of the injection. Movement of the piston also produces vibrations at the start and stop. FIG. 7 illustrate the frequency domain and time domain of the start sound on the upper left and lower left, respectively, and the frequency domain and time domain of the finish sound on the upper right and lower right, respectively. FIG. 8 shows the preferred locations of sound sensor 22 and vibration sensor 24. As shown in FIG. 9, a microphone can be used as the sound sensor, and an accelerometer, such as those included in smart phones, can be used as the vibration sensor. Accelerometers can measure rotations and translations in three directions along a Cartesian coordinate. Traces of the movements and sounds detected are also shown in FIG. 9. The movement trace shows two distinct spikes of short duration indicating the start and stop of the injection. The sound trace also shows two similar distinct spikes of short duration indicating the start and stop of the injection. The movement and sound start spikes and the movement and sound stop spikes indicate the start and stop of the injection and the overlapping of the start spikes and of the stop spikes reaffirms or confirms the start and stop time of the injection.

To minimize false positive from external noise, e.g., human voices, household noises, picked up by the sound sensor and false positive from external movements, e.g., patients' handling of the eAdaptor, by the vibration sensor, switch 44 of eAdaptor 10 can be utilized to delimit the window that the sound sensor and vibration sensor active to sense sound and movement, respectively. This means that only when AI 30 is fully inserted into eAdaptor 10 to activate switch 44 would eAdaptor 10 wakes up and be prepared to detect sounds and movements. High-pass, low-pass and/or band-pass filters can also be used to minimize background noise and vibrations. Another methodology is to create inbuilt tactile vibrations at the start and end of the injections and the sensors are designed to pick up those tactile signals within the specified amount of time.

Combining the sound sensor and the vibration/movement sensor, as illustrated in FIG. 9, and minimizing external and/or environmental sources produce a robust combination sensor. Matching the overlapping sound and vibration spikes, discussed above, further minimize false positive and yield reliable start and stop time of injection. Matching the sound and vibration frequencies/wavelengths, pitches and other characteristics, such as routine or planned delays, to the expected values can also be used to improve the detection of start and stop time of injection.

Figure 10:
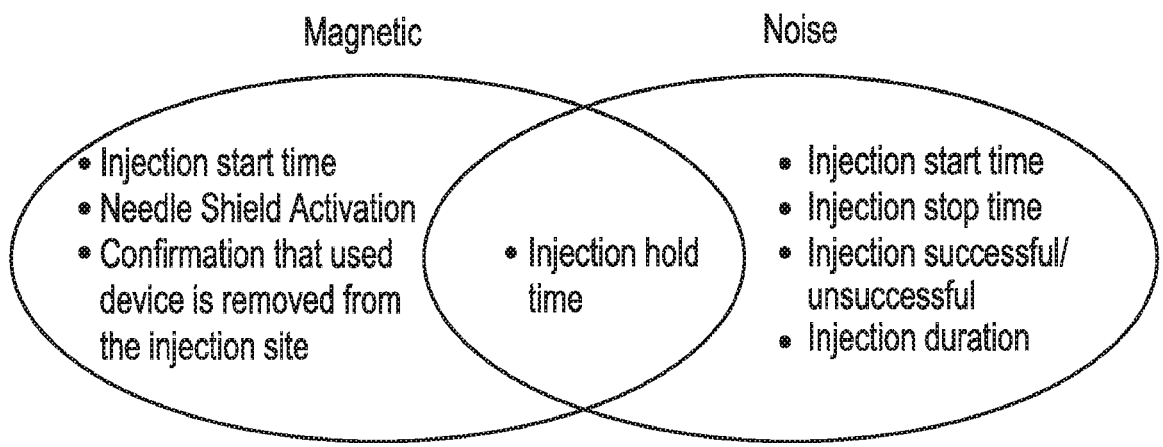
FIG. 10 is a Venn diagram showing properties sensed by the magnetic, sound and vibration sensors.

According to another aspect of the present embodiment, the magnetic/proximity sensor system and sound/vibration sensors can be used in combination to yield additional AI information. As best shown in FIG. 10, the magnetic sensor system discussed above yields the injection start time (left end of segment B in FIG. 6), the activation of front shield 34 (segment A in FIG. 6) and the time that the used AI is removed from the activation site (right end of segment B in FIG. 6). The sound and vibration sensors yield the injection start time and injection stop time (overlapping spikes in FIG. 9), the duration of injection time (time between said spikes) and whether the injection was successful (the existence of the stop injection spike or whether the duration of injection time is within an acceptable range). Additionally, the combination of these two sensor systems also yields the injection hold time, recommended by the IFU to prevent a wet injection (noticeable wetness on the skin at injection site indicating less than complete injection). The injection hold time can be visually illustrated as the time duration of segment B in FIG. 6 from the magnet sensors minus the time duration between the start and stop spikes in FIG. 9 from the vibration or sound sensor. FIG. 10 shows that the inventive eAdaptor can use the sensors in combination, as shown by the overlapping portion of the Venn diagram, and can use the sensors individually to obtain data.

Other information can also be extracted from the sensors in eAdaptor 10. For example, whether lock sleeve 40 is locked to prevent reuse can be ascertained by determining whether segment C in FIG. 6 extends below the lowest point of segment A, i.e., confirming that lock sleeve 40 travels beyond its starting position.

AIs that do not have a NFC label or identification code, discussed above, may also be used with the inventive eAdaptor 10. The logic/software that operates eAdaptor 10 would detect that the AI does not have such label or code and may ask the patient or HCPs to manually enter the relevant AI information into the smart phone either before or after the injection. Alternatively, the eAdaptor or the smart phone may display a message advising the patients to discard this AI and only use AIs that have n NFC label or a readable identification code.

AIs that do not have magnetic members 54 but has a NFC label or identification code can be used with the inventive eAdaptor 10, but no information obtained by the magnetic sensor system can be obtained and only information obtained by the sound and vibration sensors can be obtained. AIs that do not have either a NFC label/identification code or magnetic members 54, e.g. unaltered conventional AIs, can still be used, as described above, i.e., AI information should be entered manually and sound and vibration sensor data can be obtained.

In situations where a smart phone or smart tablet or another connectable computing device is not available to communicate and receive injection data from eAdaptor 10, the electronics of eAdaptor 10 may include a memory or data storage device, such as flash memory, flash drive, EEPROM, EPROM to store the injection data preferably with unique markers, so that multiple sets of injection data can be stored and distinguished from each other. When a smart phone is available, the stored data can be transmitted to the smart phone or to another destination, such as the internet cloud storage.

In accordance with another aspect of the present invention, AI 30 can be inserted into eAdaptor 10 at any orientation without negatively affecting the operations of the magnetic sensor system. AIs generally have a cylindrical shape with circular, oval or polygonal cross section. The locations of magnet sensors 20 on the eAdaptor relative to the locations of the magnetic member 54 should correspond to each other or should be proximate to each other in order to obtain strong or readable magnetic fields when they approach each other. The present inventors have invented an arrangement such that at least one magnetic member 54 is brought close to at least one magnetic sensor 20 at the start of the injection to create a readable magnetic signal therebetween.

Figure 11:
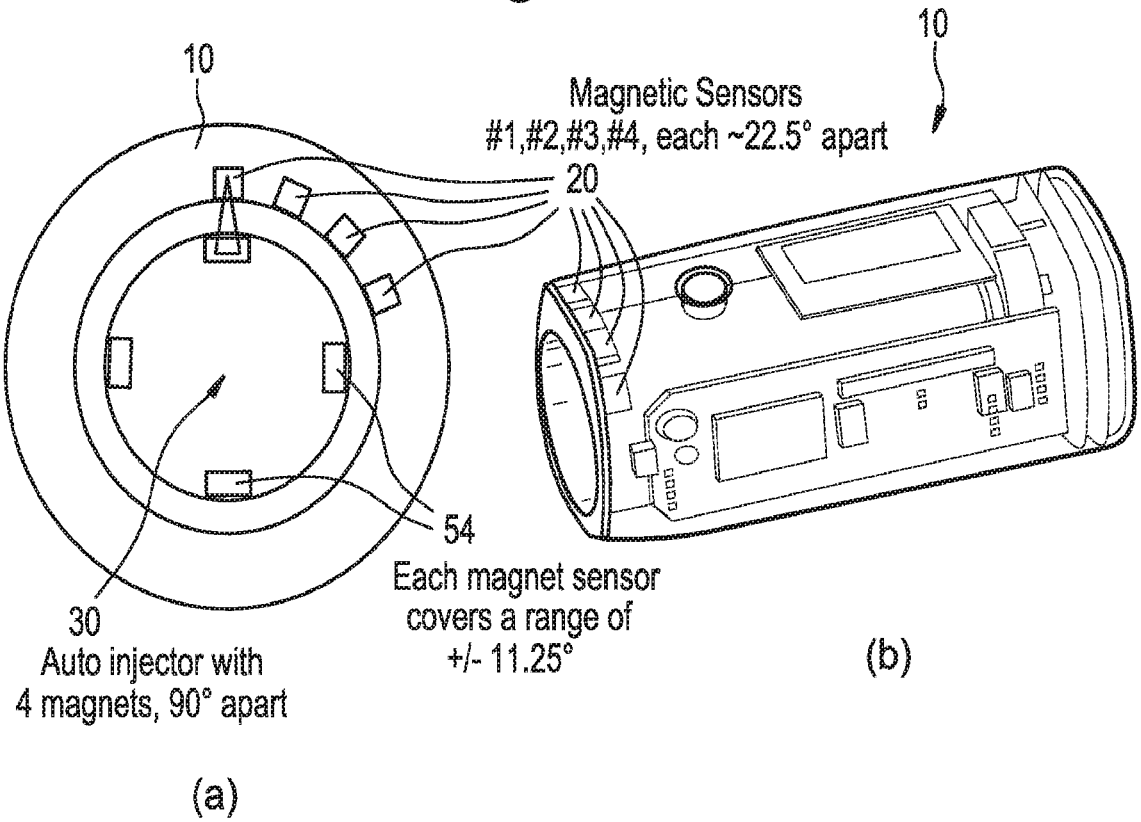
FIG. 11a is a cross-sectional, schematic view of the interaction between the AI's magnetic members and the eAdaptor's magnetic sensors.
FIG. 11b is a perspective view of the eAdaptor with the housing skin shown in transparency to illustrate the magnetic sensors.

A non-limiting illustration of this orientation independence is illustrated in FIGS. 11a-11b. In this illustration, AI 30 has four (4) magnetic member 54 evenly located around the perimeter of lock sleeve 40 or about 90° apart, as shown in FIG. 11a, at 12 o'clock, 3 o'clock, 6 o'clock and 9 o'clock. Magnetic sensors 20, which can cover an angle of about 22.5° (or ±11.25° from a centerline are located about 22.5° apart from each other on the perimeter of eAdaptor 10. As illustrated, four magnetic sensors 20 are deployed and cover an angular arc of about 67.5° out of 360°. The 67.5° arc, when added to the 11.25° range of the left side of the left most magnetic sensor 20 and to the 11.25° range of the right side of the right most magnetic sensor 20, yields a 90° coverage. As shown in FIG. 11a, magnetic member 54 located at 12 o'clock forms a magnetic field with the left most magnetic sensor.

Figure 12:
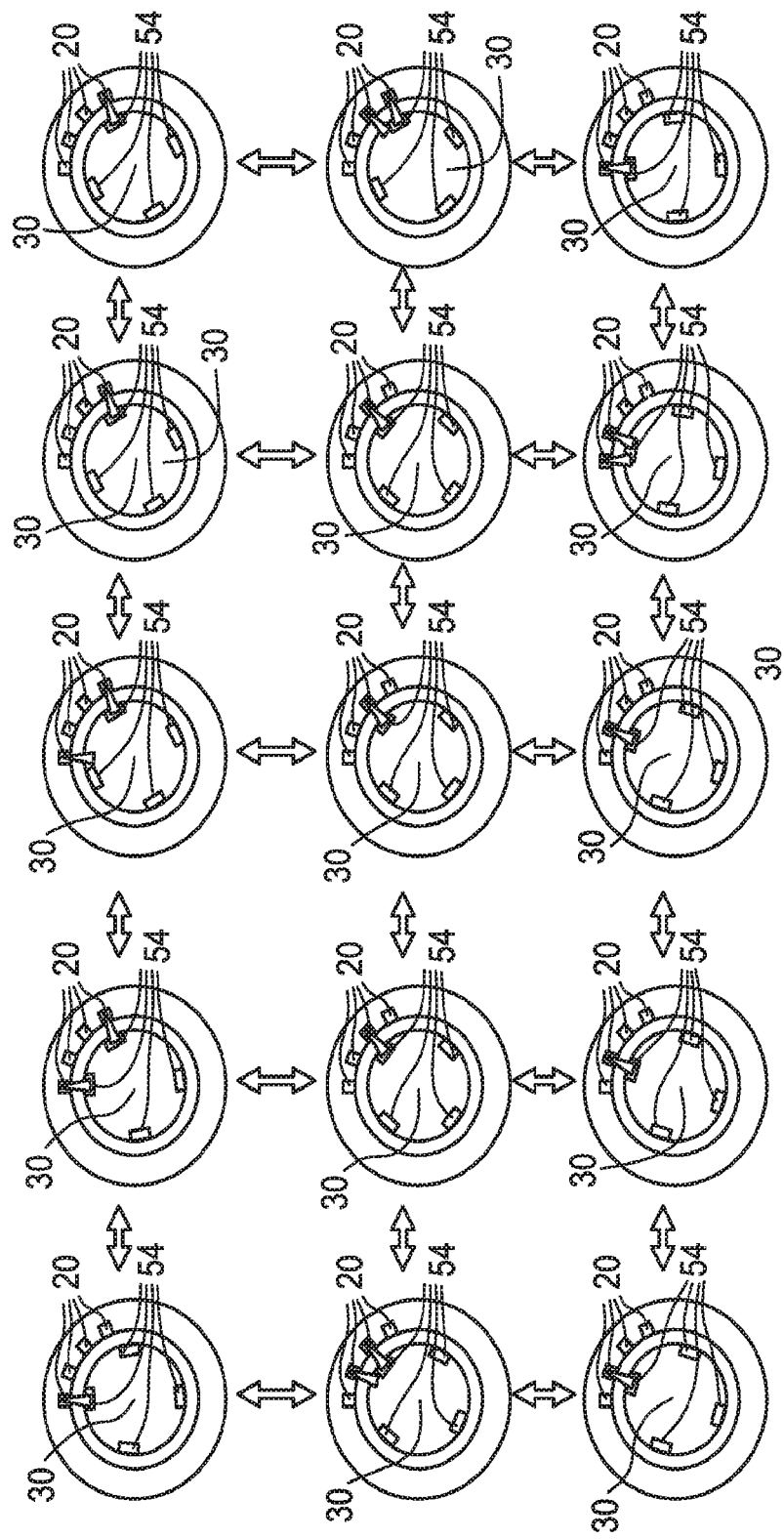
FIG. 12 show various relative orientations between the AI and the eAdaptor of FIG. 11a to illustrate the orientation independence of the inventive magnetic sensor system.

FIG. 12, which shows fifteen (15) different angular orientations between AI 30 and eAdaptor 10, illustrates the orientation independence of the present invention. The fifteen different orientation are referred by two indices (i, j) which are the row number and column number, respectively. FIG. 12(1, 1) is similar to the orientation shown in FIG. 11a discussed above. As AI 30 rotates slightly counterclockwise to FIGS. 12(1, 2) and 12(1, 3), the left most and right most sensors 20 sense the magnetic members 54 originally at 12 o'clock and 3 o'clock. Additional counterclockwise shown in FIGS. 12(1, 4) and 12(1, 5) show that the right most sensor 20 maintains magnetic contact with the magnetic member originally located at 3 o'clock.

After the AI is rotated about ⅛ of a revolution (about 45°) counterclockwise, the magnetic member originally located at 3 o'clock is sensed by both of the middle magnetic sensors 20, as shown in FIG. 12(2, 1). Additional rotation in the counterclockwise direction would bring the magnetic member 54 originally located at 3 o'clock to be sensed by the second left most magnetic sensor, as shown in FIGS. 12(3, 1), 12(3, 2) and 12(3,3). Additional counterclockwise rotation, such that the total rotation is close to 90°, would bring the magnetic member 54 originally located at 3 o'clock to be sensed by the two left magnetic sensors, as shown in FIG. 12 (3, 4). When the counterclockwise rotation is about 90°, the magnetic member 54 originally located at 3 o'clock is positioned at about 12 o'clock, similar to the initial orientation at FIG. 12(1, 1), and the orientation process repeats.

Referring back to FIG. 12(2, 1), if the AI is rotated in the clockwise direction instead, then the magnetic member 54 originally located at 3 o'clock would be sensed by the second right magnetic sensor 20 as shown in FIGS. 12(2, 2), 12(2, 3) and 12(2, 4). Continuing clockwise rotation as shown in FIG. 12(2, 5), the magnetic member 54 originally located at 3 o'clock is sensed by the two right magnetic sensors 20.

Hence, FIG. 12 illustrate that at any orientation, AI 30 is sensed by at least one magnetic sensor 20. Those of ordinary skills in the art can apply the teachings of the present inventors to change the number of magnetic sensors 20 on eAdaptor 10 and the number of magnetic members on AI 30 and still be within the scope of the present invention. For example, if sensors 20 are located at about 22.5° apart and cover the entire perimeter of eAdaptor 10, then only one magnetic member 54 is required on the AI, and the reverse is also true. In another example, if two magnetic members 54 are positioned at about 180° apart, then eight (8) sensors 20 should be deployed at about 22.5° apart to cover (180°-22.5°). Given the angle or arc, which can be any angle, that each magnetic sensor 20 can sense, those of ordinary skills in the art can select the proper number of sensors 20 and magnetic members 54.

AIs may have outer diameters that are significantly smaller than the inside diameter of eAdaptor 10. Hence to ensure that the magnetic members 54 on the AI are positioned as closed to the magnetic sensors 20 on the eAdaptor as possible, at least one and preferably two leaf springs 28, as best shown in FIG. 3, push AI 30 towards the bank of magnetic sensors 20. As shown in FIG. 13, springs 28 push AI 30 towards magnetic sensors 20 on eAdaptor 10.

In accordance to another aspect of the present invention, when not in used eAdaptor 10 can be mated to a secondary structure, such as a battery 56, as shown in FIGS. 14a-14b. Battery 56 can also be used to charge the smart phone to increase its functionality. Other secondary structures can be a blood glucose meter, a spirometer, a flash memory stick, a portable speaker, etc. when equipped with the right connectivity universal interface that can connect to the eadapter The electronics of eAdaptor 10, which are electrically connected to PCB 26, are schematically shown in FIG. 15. The firmware/software, instructions to operate eAdaptor 10 and RAM memory are stored in microcontroller 58. It is noted that in FIG. 15 double arrows indicate two-way communication or data/instruction transfers and single arrows indicate the one-way direction of communication, control or data transfer. Aforementioned components, such as digital screen 16, vibration sensor 24, magnetic sensor(s) 20, sound sensor 22 with injection start sensor(s), such as the magnetic sensor and the sound/vibration sensors and stop sensor(s), such as the sound/vibration sensors, temperature sensor 18, NFC reader 50 and NFC tag 48, are shown connected to microprocessor 58. Other components are also connected, such as Bluetooth module 60 to connect to the smart phone, a speaker 62 to issue sound warnings and such to the patients, a power supply 64 which can be recharged by an external source through a USB port 66 and a charging circuit 68. eAdaptor 10 may also have one or more color LED lights 70 to communicate information to the patients, such as battery status, injection status and Bluetooth connectivity. eAdaptor 10 may also have a debugging port 72 for technicians to diagnose potential problems with the device.

II. The Internal Logic and/or APP That Captures Injection Information and Provides User Feedbacks As used herein, internal logic 100 refers to the software or firmware, which includes computer instructions and programming that reside in eAdaptor 10, specifically on PCB 26 and more specifically on microprocessor 58 and on the individual electronic components illustrated in FIG. 15, if any. An application or APP refers to software, which includes computer instructions and programming that reside on the smart device 250, which can include a smart phone or smart tablet or other computing device with wireless connectivity. The APP is designed to work with the internal logic to receive information or data from the eAdaptor to process, calculate and manipulate same. The APP may also display messages with more details including texts than the messages that are displayed on digital screen 16 on eAdaptor 10. Smart device 250 preferably has the capability to store the data collected by eAdaptor 10 and the results calculated from said data, and is also able to transmit such data and results to another computing device or Internet storage cloud. Preferably, internal logic 100 can operate the eAdaptor and the AI independently without the APP, since eAdaptor 10 may function without a smart device 250.

Figure 16:
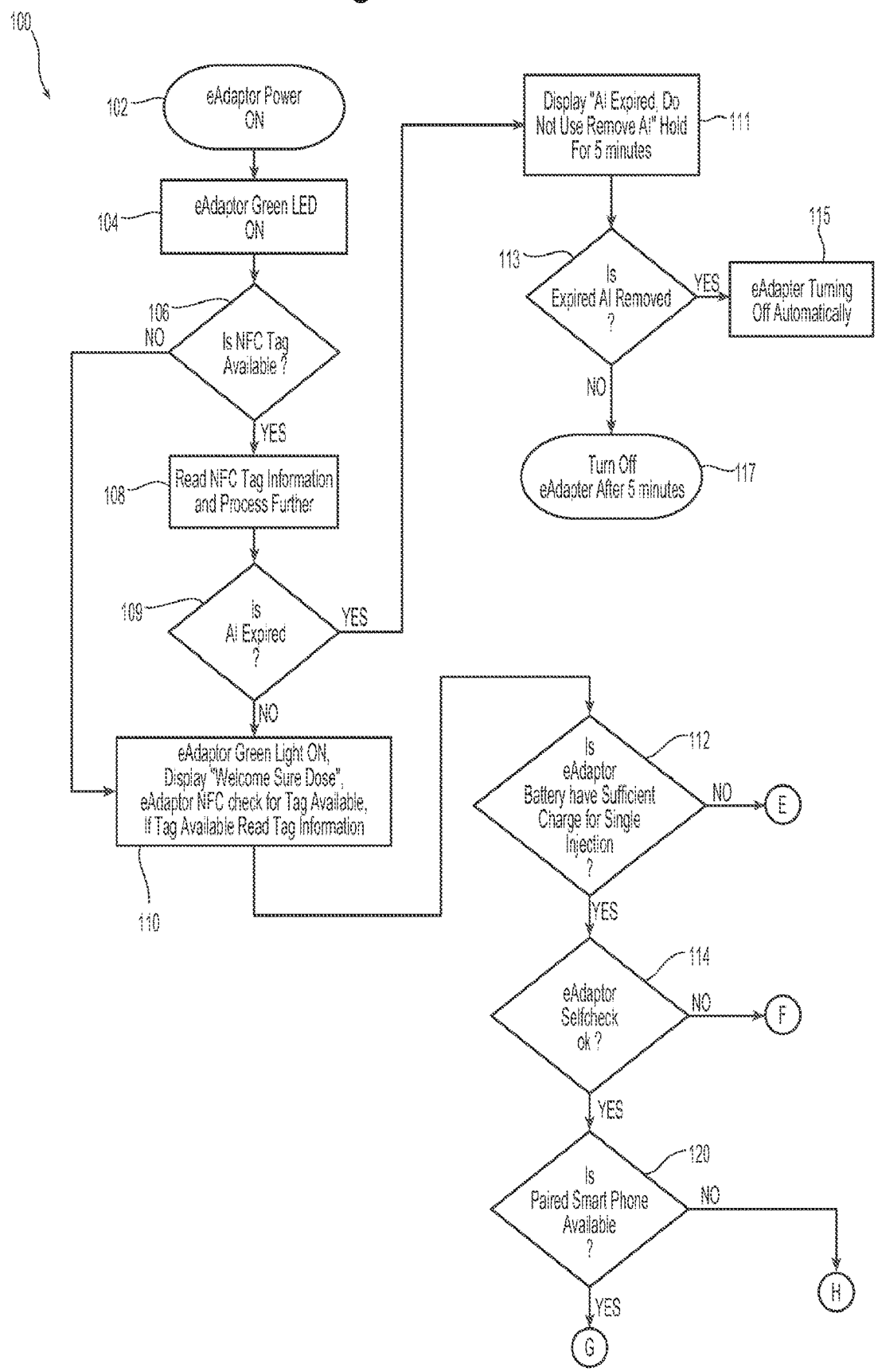
FIG. 16 and its subparts show a flow chart of the internal logic operating the inventive eAdaptor.
Figure 16:
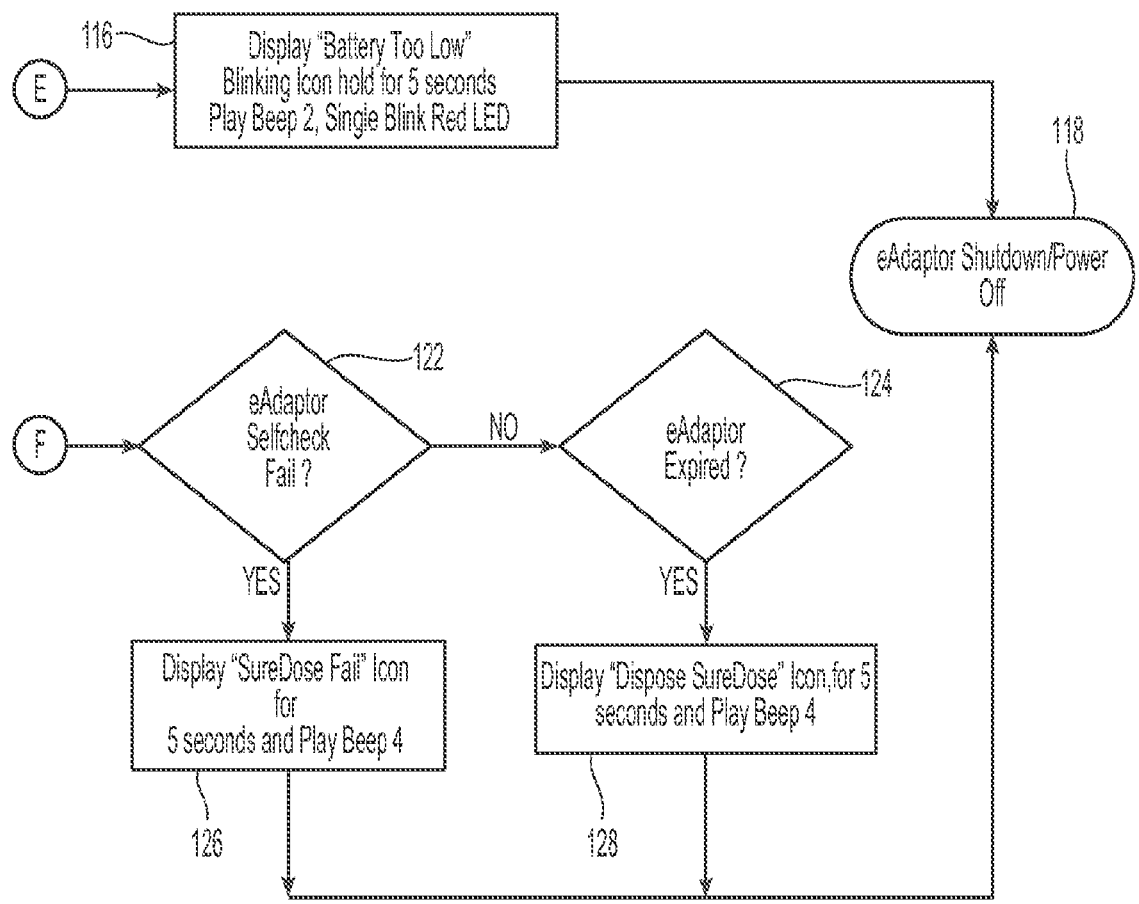
Figure 16:
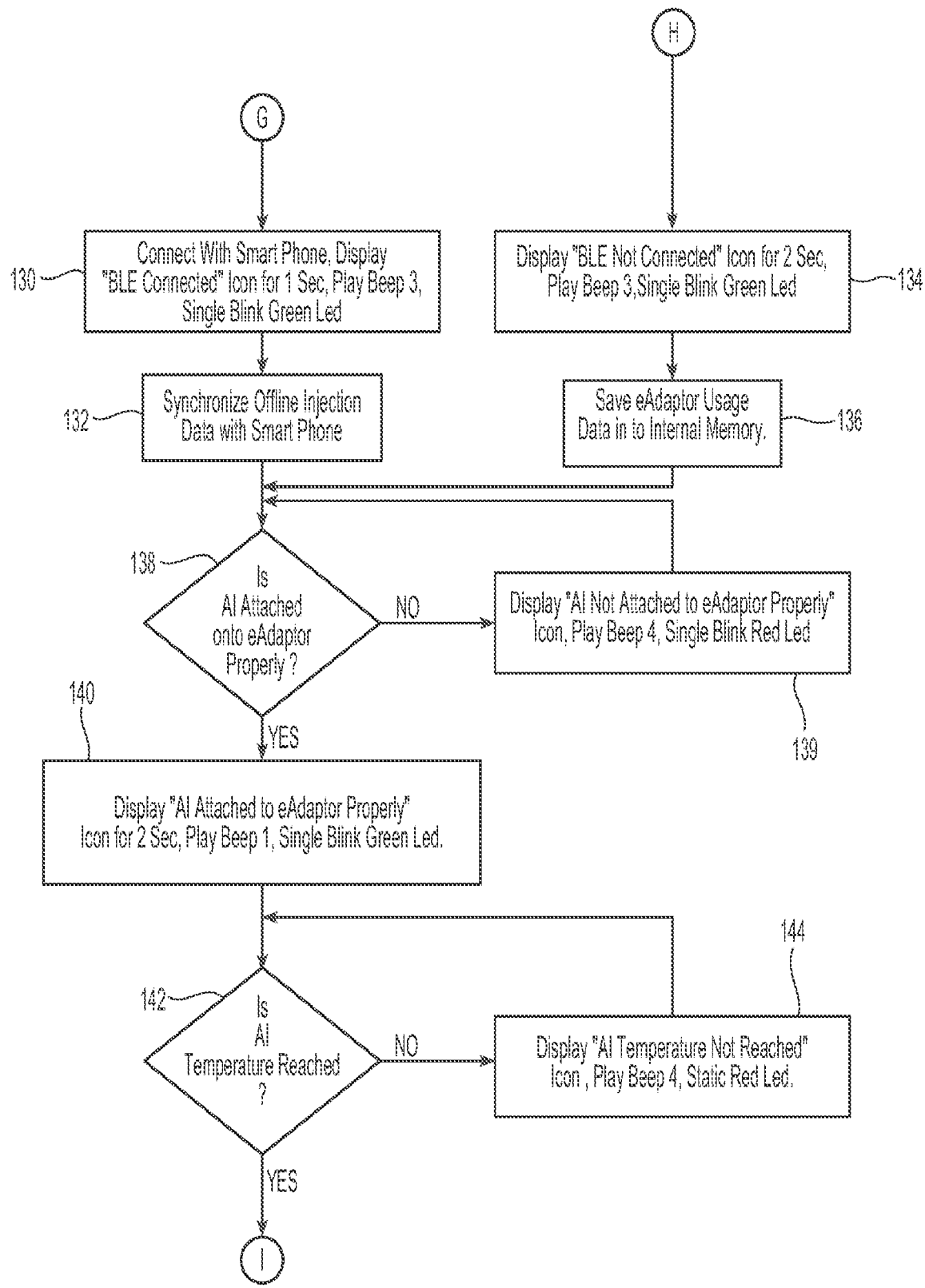
Figure 16:
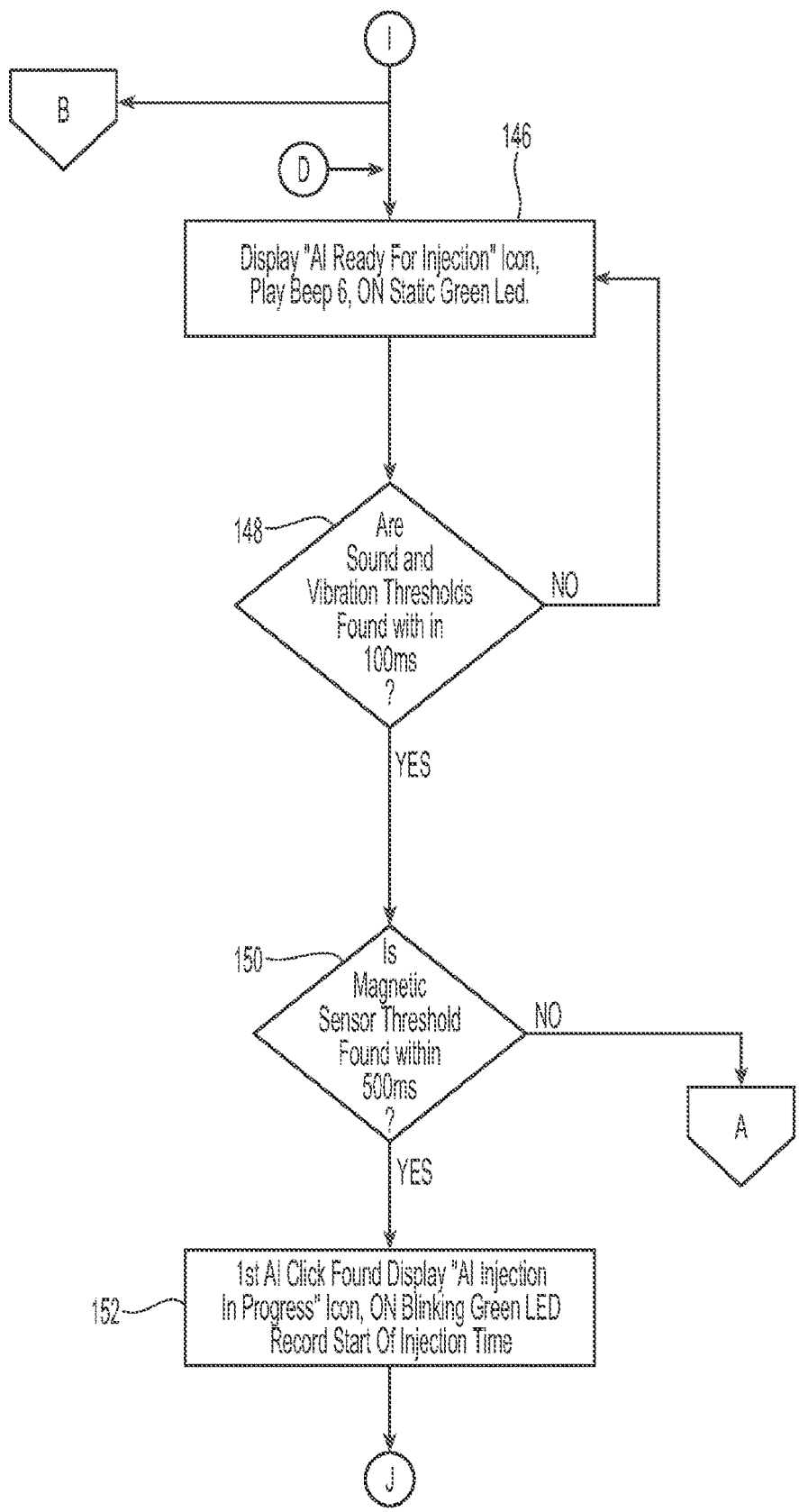
Figure 16:
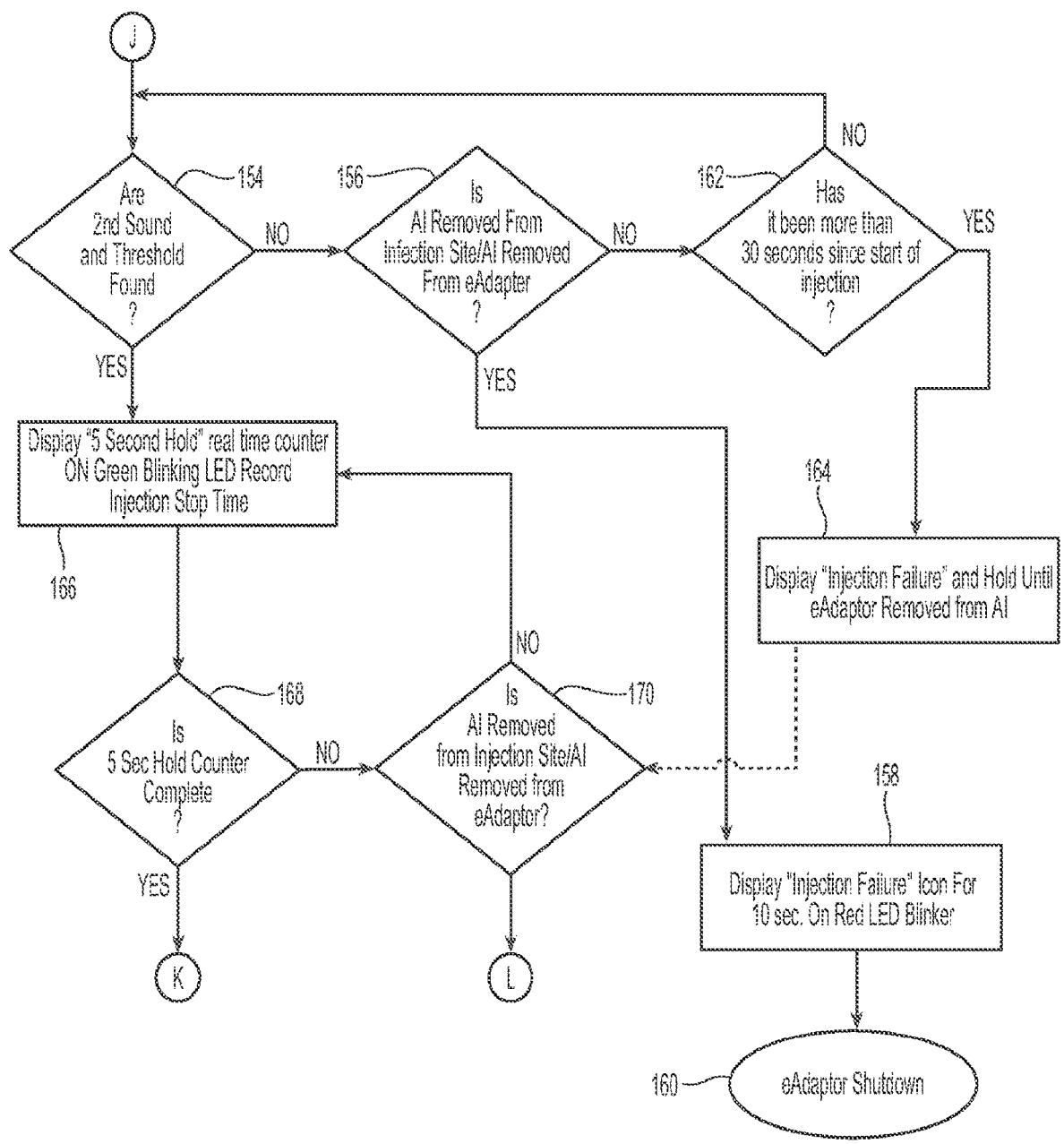
Figure 16:
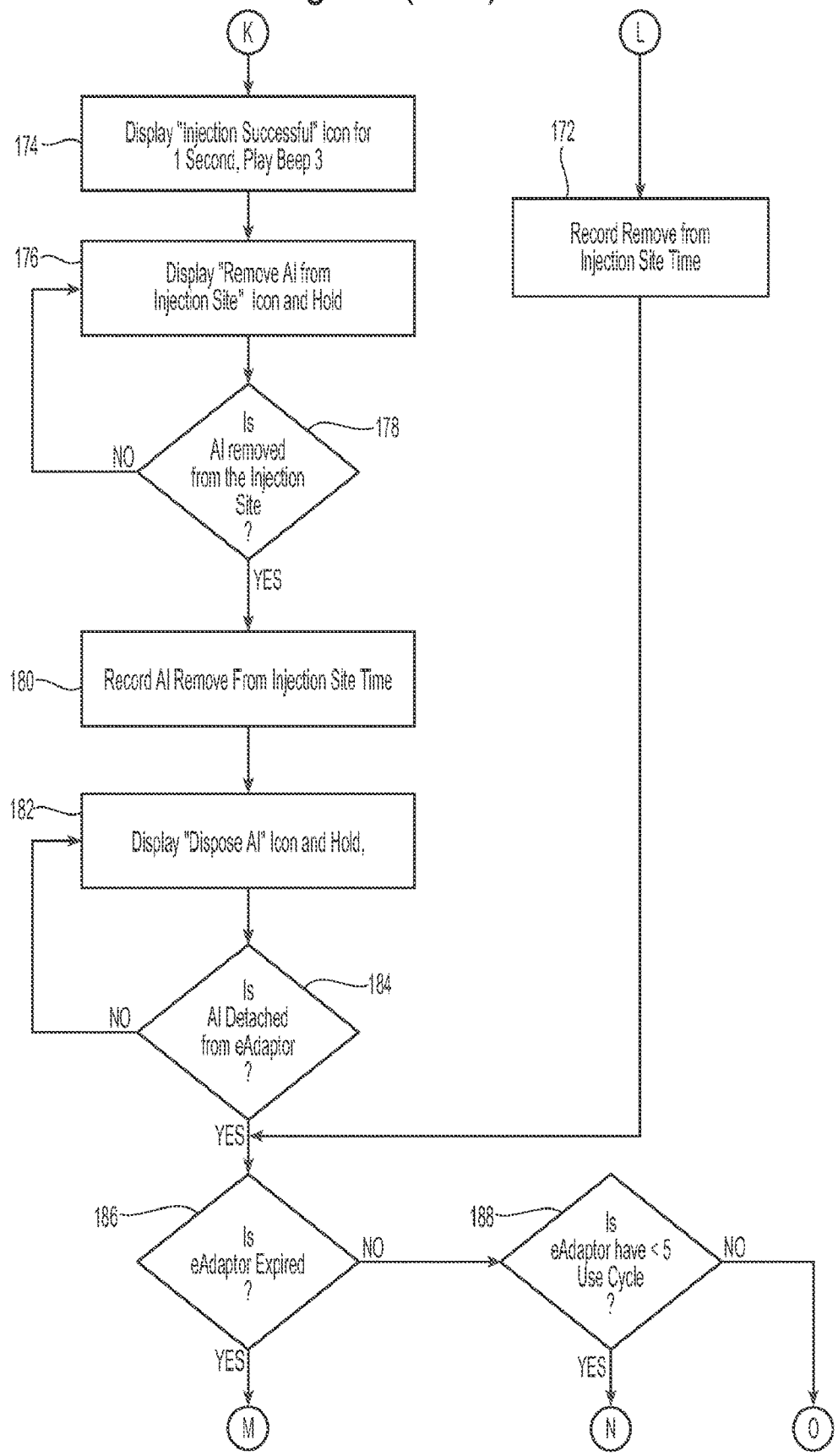
Figure 16:
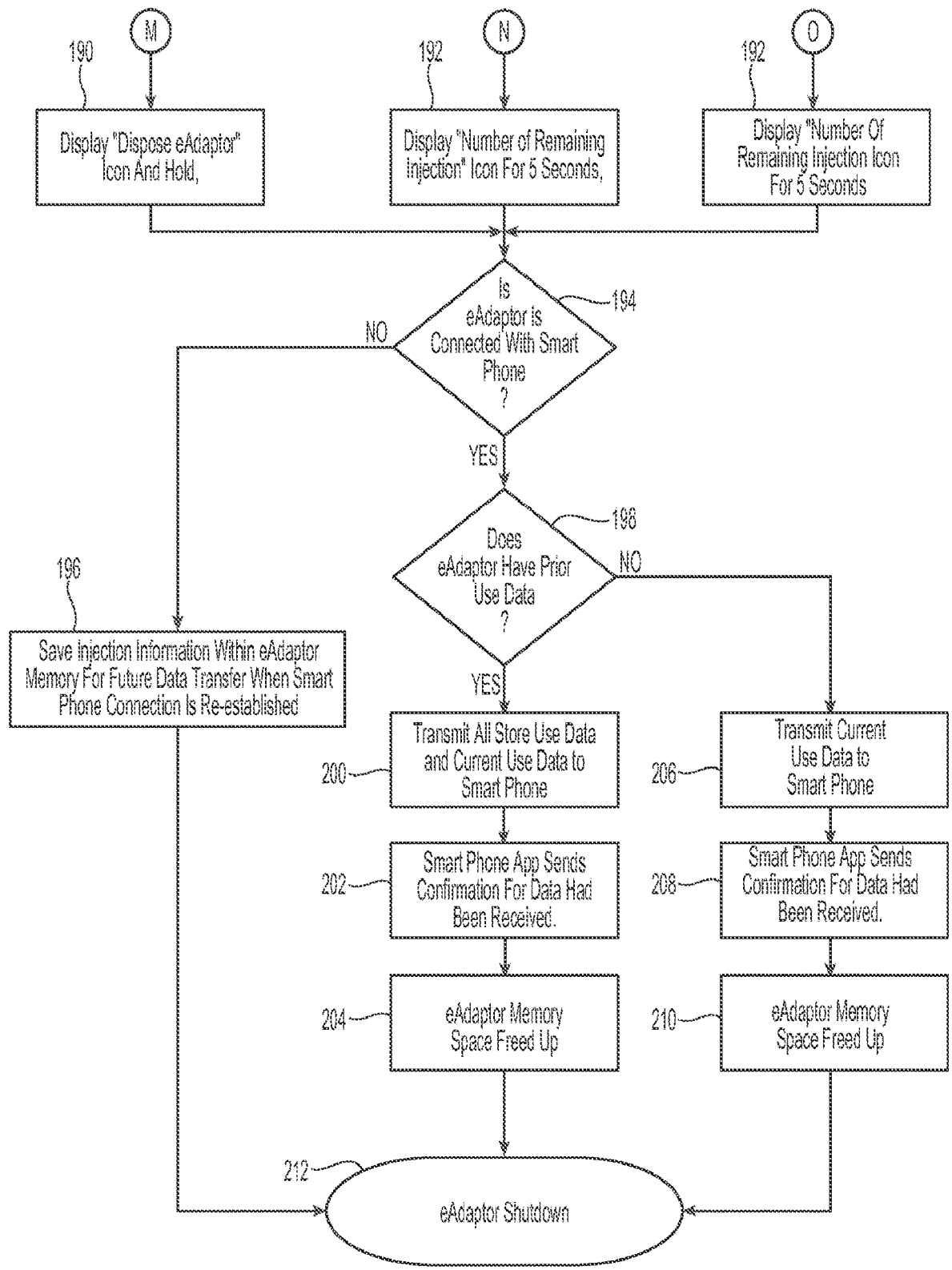

The internal logic or operating instructions of eAdaptor 10 are illustrated in FIG. 16 and its subparts. Internal logic or logic 100 comprises the steps and Boolean decisions that operate the eAdaptor and the linked smart phone. It is noted that the APP that runs on the paired smart phone are different than logic 100 but work in conjunction with logic 100. Logic 100 preferably starts when eAdaptor is powered on at step 102 by AI 30 being inserted into the eAdaptor and making with contact switch 44, discussed above. Preferably, a green LED light 70 is illuminated to indicate the ON status in step 104. Logic 100 would first determine whether AI 30 has a NFC tag 48 at decision point 106. If a NFC tag or another identification code, such as a bar code or the like, is present, NFC reader 50 reads the AI information contained therein at step 108. Preferably, a decision point 109 after step 108 determines whether the AI has expired, which is discussed further below, and if the AI has expired logic 100 displays message 111 to the patients and asks the patients to remove the expired AI. When the patients remove the expired AI, the eAdaptor automatically turns off at step 115 due to switch 44 turning off without an AI inserted. Decision point 113 determines that if the patients do not remove the expired AI, then the eAdaptor shuts itself down after an amount of time at step 117. As discussed in connection with logic 100, "screen" includes digital screen 16 on eAdaptor 10 and the screen on the smart phone. Even if the AI does not have a NFC tag or another identification code, logic 100 also advances to step 110.

If the AI has not expired, the green LED (or any visual indicator) is again illuminated and the screen displays a message confirming the AI in step 110. Next, logic 100 determines whether it has sufficient battery power to conduct the operation is decision point 112. If battery power is sufficient, logic 100 advances to decision point 114 for the eAdaptor to self-check. The self-check may include but is not limited to detecting all the sensors and electrical components in the eAdaptor. If the battery power is insufficient, logic 100 would display a message and/or illuminate a red LED and/or play a beep from speaker 62 at step 116 and shuts down the eAdaptor at step 118. If the self-check at step 114 is affirmative, logic 100 advances to decision point 120 to determine whether the paired smart phone is available. If the self-check at step 114 is negative, then logic 100 advances to determine whether the self-check fails or whether eAdaptor 10 has expired at decision points 122 and 124, respectively. Failure messages 126 and 128 would be displayed if eAdaptor 10 had failed or expired, respectively, before logic 100 shuts down eAdaptor 10 at step 118.

If logic 100 detects a paired smart phone, eAdaptor 10 is connected to the smart device at step 130, and appropriate sounds and LED color lights communicate to the patients that Bluetooth connection to the smart device has been established. Thereafter, logic 100 advances to the synchronizing of any stored/offline injection data with the smart phone in step 132. If logic 100 does not detect a paired smart phone, a message is displayed on screen 16 and appropriate sounds and LED color lights communicate to the patient that there is no Bluetooth connection at step 134, and the injection data would be saved to memory at step 136.

Regardless of whether a paired smart phone is detected, logic 100 advances thereafter to decision point 138 to determine whether AI 30 is property attached to eAdaptor 10, for example by sensing whether switch 44 is fully or partially activated by the insertion of AI 10. If the AI is not properly attached, a message is displayed and sounds and LED color light are communicated to the patients in step 139. Logic 100 then performs a repeat loop until the AI is properly attached, as shown. After the AI is properly attached to the eAdaptor, a message is displayed and sounds and LED color light(s) are communicated to the patients in step 140. These communication means to the patients are relevant for proper device usages from a regulatory standpoint.

Thereafter, logic 100 checks whether the AI has reached room temperature in decision point 142 using temperature sensor 18, discussed above. If the AI's temperature is not yet reached, a message is displayed and sounds and LED color light are communicated to the patients in step 144. Logic 100 then performs a repeat loop until the AI's temperature is reached, as shown. After the AI's temperature is reached, a message is displayed and sounds and LED color light are communicated to the patients in step 146 that the AI is ready for injection.

At this point, the sensors are prepared to sense the sounds, vibration and the variation of magnetic fields associated with the injection. At decision point 148, logic 100 determines whether threshold sound and vibration levels have been sensed. If not, logic 100 performs another repeat loop until the sound and vibration thresholds are sensed. Threshold sound and vibration levels can be the sound and movement at the start of the injection or other threshold levels. Once these thresholds are sensed, logic 100 determines whether a magnetic threshold reading, which can be the magnetic reading at the start of the injection or other magnetic readings, has been sensed at decision point 150. If magnetic sensors 20 on eAdaptor 10 cannot detect a threshold magnetic reading substantially contemporaneously with the detection of the sound and vibration threshold readings, then logic 100 would treat the AI as having no magnetic capability and logic 100 would execute a separate set of instructions labeled as branch "A" and discussed below.

If a threshold magnetic level is sensed, then the first sound/click from the AI would be sensed by the sound and vibration sensors 22 and 24 at step 152, and a message is displayed that the injection has begun along with associated sounds and LED color lights. Logic 100 would also record the start time/date of the injection. Next, the second sound and vibration indicating the injection stop should be sensed at decision point 154. If no second sound and vibration are sensed, then logic 100 would check with the magnetic sensor system to determine whether the AI has been removed from the injection site as discussed above in connection with FIG. 6 at decision point 156. If the AI has been moved from the injection site, then logic 100 would display an error message and illuminate a red LED at step 158 and shuts down eAdaptor 10 at step 160. If the AI has not been moved from the injection site, logic 100 would need to determine whether a predetermined amount of time has elapsed, e.g., 15 seconds, 20 seconds, 30 seconds, etc., in step 162 by checking with the RTC. If the predetermined wait time has not expired, then logic 100 executes another repeat loop, as shown, to wait for the second sound and vibration. If the predetermined wait time has expired which can mean that the AI had stalled and the second click sound and vibration were not heard/sensed, then logic 100 displays a message of injection failure at step 164 and hold until the eAdaptor and AI are removed from the injection site. Step 164 may be connected to decision point 156 (or 170 discussed below) to allow for an orderly shutdown of the eAdaptor.

If the second sound and vibration indicating the injection stop are sensed at decision point 154, then at step 166, the injection stop is recorded and display 16 or the smart phone's display should also ask the patients to hold the AI and eAdaptor at the injection site for a predetermined amount of time, e.g., 5 seconds, 10 seconds, etc. Logic 100 then checks to ensure that the hold time is adequate at decision point 168. If not, then logic 100 may run another repeat loop until the hold time is met and determine whether the AI has been removed from the injection site or removed from the eAdaptor at decision point 170. If the hold time is not kept or satisfied and the AI has been removed from the injection site, then logic 100 executes step 172 to record the time of premature removal from injection site.

If the hold time was kept or satisfied, then eAdaptor would display a display of successful injection at step 174 and another display at step 176 to instruct the patients to remove the AI from the injection site, i.e., their skin. Logic 100 then determines whether the AI is removed at decision point 178, i.e., segment C in FIG. 6. If the AI has not been removed, logic 100 can run another repeat loop until the AI is removed and then record the AI removal time at step 180. Logic 100 would then display a message to the patients to remove and discard the AI at step 182. Logic 100 then determines whether the AI is detached at decision point 184, i.e., switch 44 is turned off. If the AI has not been removed, logic 100 can run another repeat loop until the AI is removed.

Thereafter, logic 100 rejoins step 172, as shown, to determine whether eAdaptor continues to be viable at decision points 186 and 188, where logic 100 determines whether the eAdaptor has expired. Due to life expectancies of certain electronic and mechanical components within eAdaptor 10, the eAdaptor can be safely used a number of times, e.g., up to 100 uses, 25 uses, 15 uses or 5 uses. At decision point 186, logic 100 determines whether the number of uses has exceeded the designed limit. If yes, then logic 100 displays a message at step 190 to discard the eAdaptor. If the number of uses has not exceeded the designed limit, then logic 100 determines the actual number of uses at decision point 188 and displays the number of remaining uses in step 192.

Thereafter, logic 100 determines whether the eAdaptor is connected to the smart phone at step 194. If not, then the injection data is saved to the memory on the eAdaptor at step 196. If the connection is present, then logic 100 determines if the eAdaptor has prior injection or use data at decision point 198. If there is prior use data, then logic 100 transmits all stored injection and use data, as well as the current data to the smart phone at step 200, receives a confirmation from the smart phone at step 202 and frees up memory space in eAdaptor at step 204. If there is no prior use data, logic 100 performs similar steps except that no prior use data would be transmitted in steps 206, 208 and 210. As shown in FIG. 16, after step 196, 204 or 210, eAdaptor shuts down at step 212 after a successful injection with use/injection data either stored or transmitted.

Figure 17A:
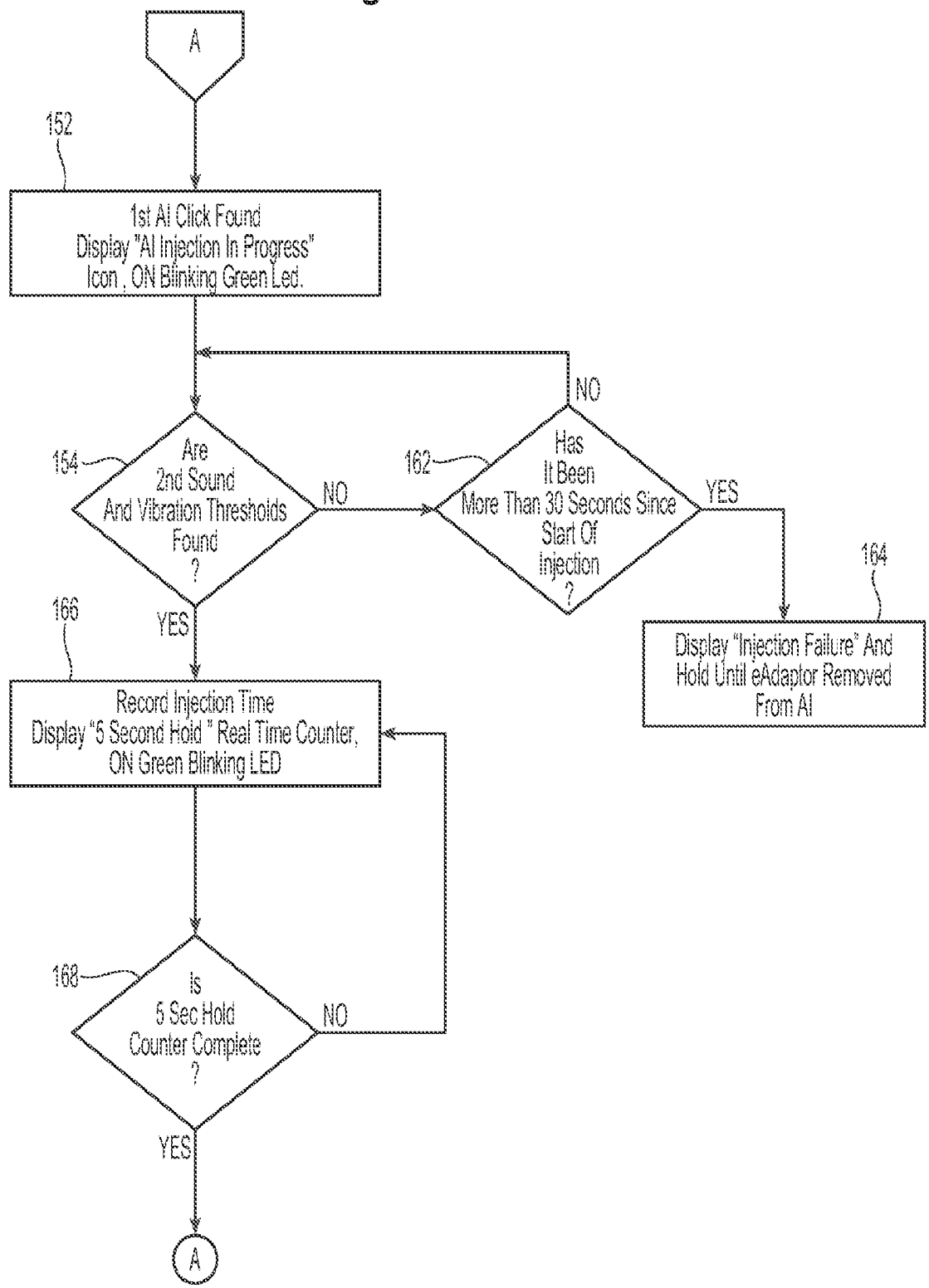
FIG. 17a and its subparts show a flow chart of a branch "A" of the internal logic of FIG. 16.
Figure 17A:
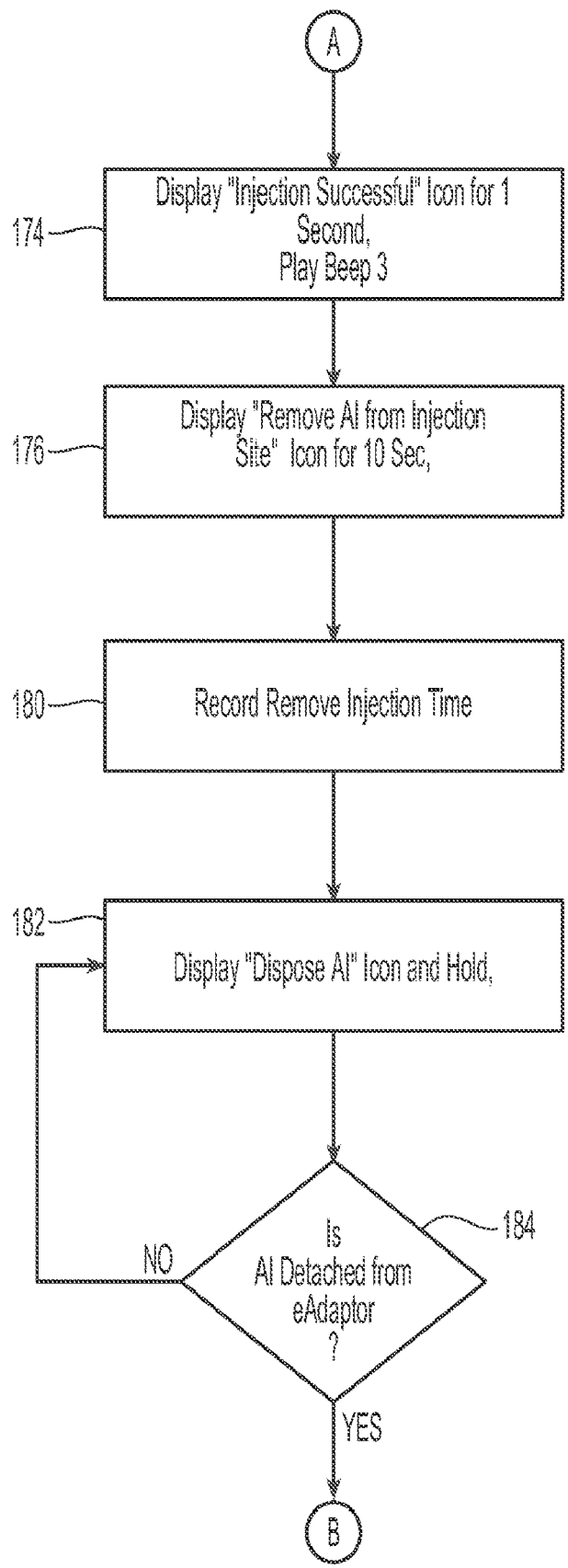
Figure 17A:
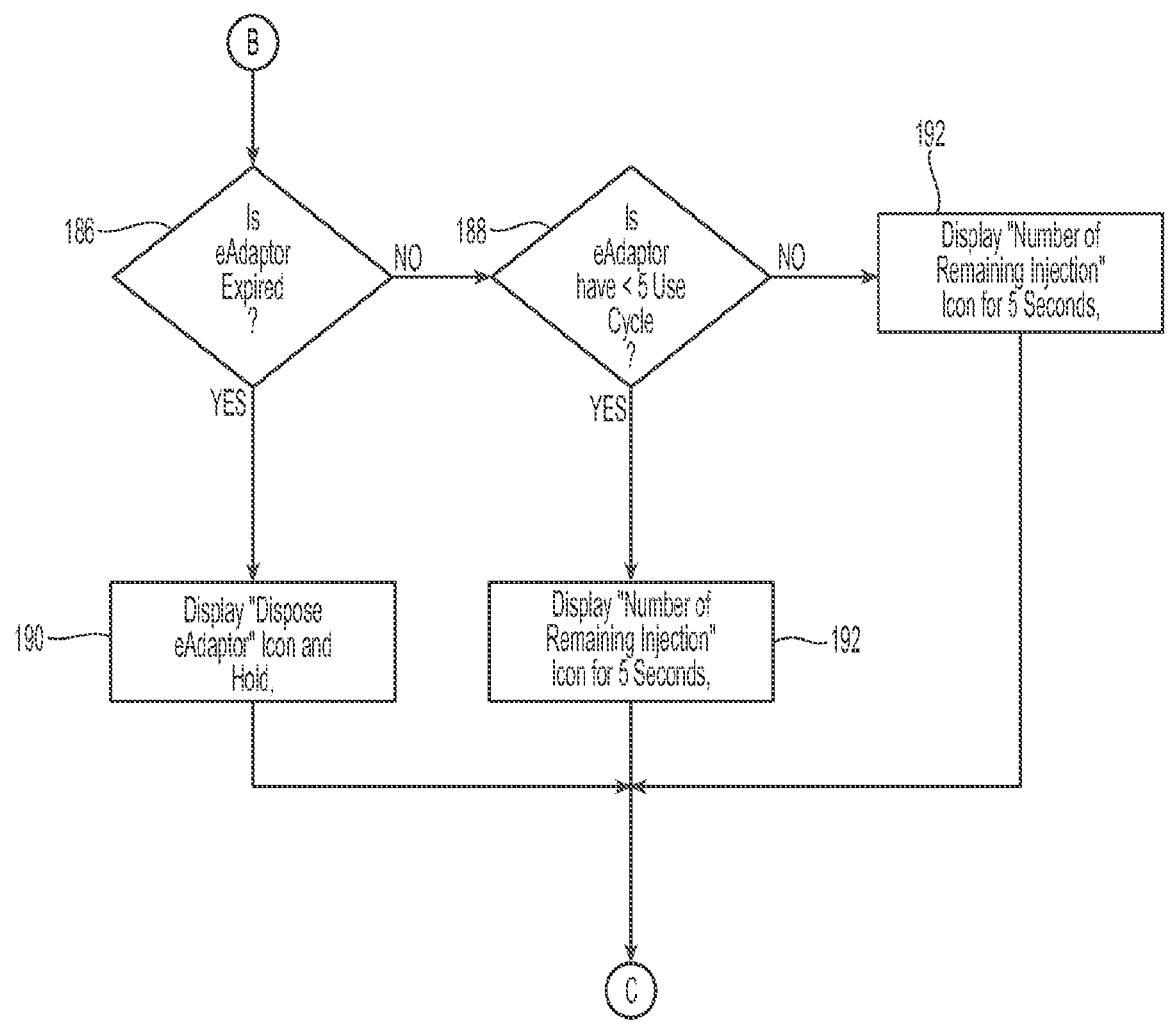
Figure 17A:
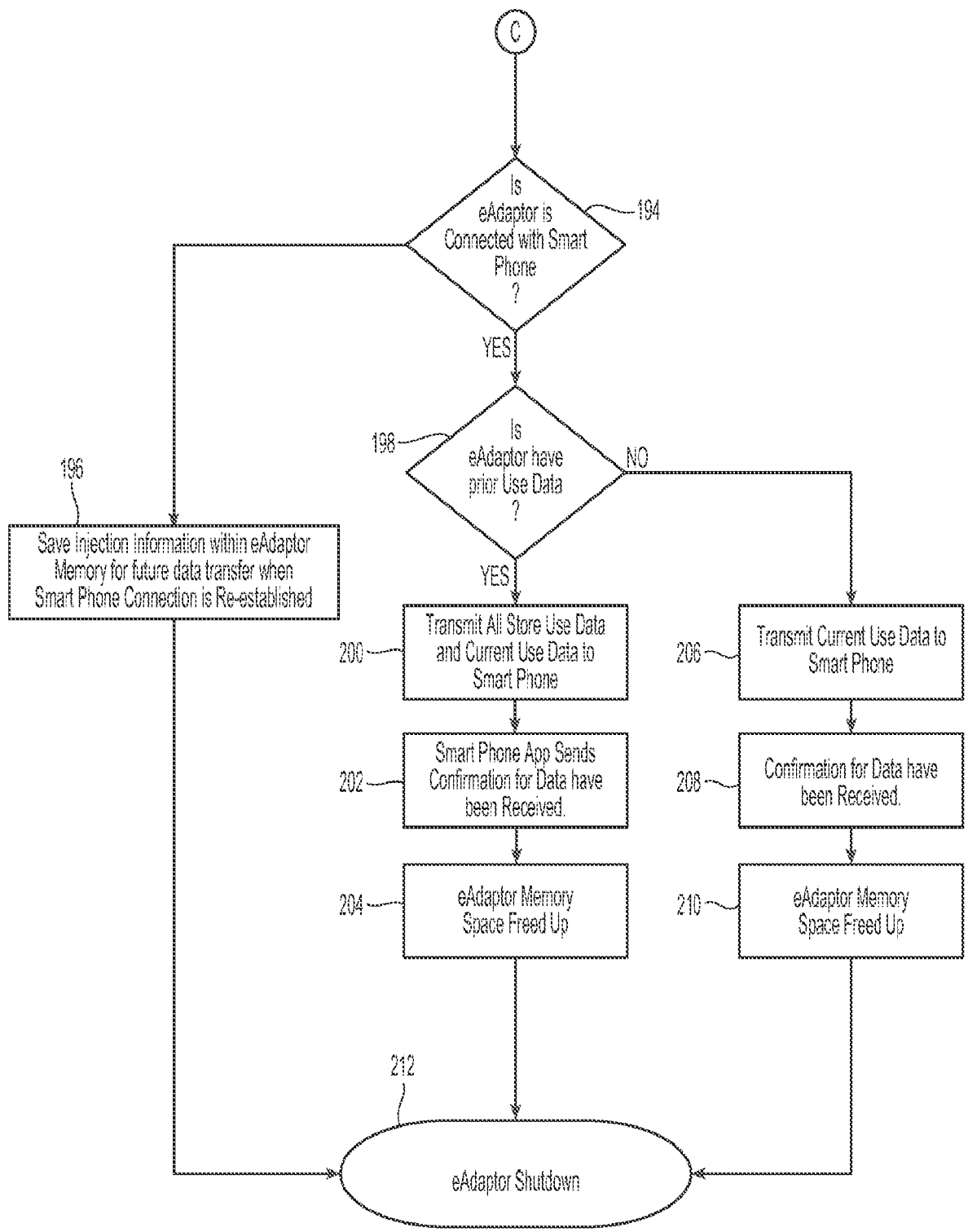

Referring back to decision point 150, when logic 100 cannot detect a threshold magnetic value, the operation of eAdaptor 10 is diverted into a different operating path, shown as branch "A" in FIG. 16. Referring to FIG. 17a, where steps and decisions that are similar to those in FIG. 16 are assigned with similar reference numbers, logic 100 would sense the first, injection start sound/vibration at step 152 and decides whether the second, injection stop sound/vibration is sensed at decision point 154. Logic 100 would then compare the elapsed time since the start of injection to a predetermined limit, e.g., 30 seconds, 45 seconds or 60 seconds, at decision point 162 and starts a repeat loop until the second sound/vibration is sensed, as shown. If the elapsed time exceeds the predetermined limit, then logic 100 would display an injection failure message at step 164. As discussed above, step 164 may be connected to decision point 156 or 170 for an orderly shutdown of the eAdaptor.

If the second, injection end noise/vibration is sensed then the injection stop time is recorded and a hold time display is shown to the patients at step 166. Logic 100 may start a repeat loop with decision point 168 until the hold time is completed, as shown. Thereafter, logic 100 may display a successful injection message and appropriate sounds and lights in step 174 and advise the patients to remove the AI from the injection site at step 176. Logic 100 would then record the AI removal time at step 180 and would display a message to dispose the AI in step 182. A repeat loop to ascertain whether the AI is detached may be executed with decision point 184.

Thereafter, logic 100 may run steps/decision points 186-212, discussed above, to determine whether the eAdaptor has expired and to transmit injection data to the smart phone, as discussed above.

Referring back to decision point 142, where logic 100 senses that the AI has reached the proper injection temperature. When the Boolean answer is "yes," logic 100 may execute a stand-alone idle loop that starts at branch "B" which is connected to decision point 142 and runs in the background when the AI is inserted. The AI's insertion was checked at decision point 138, and should the AI be removed before the idle loop is initiated the eAdaptor would be automatically shut down by switch 44. The idle loop should also runs when the accelerometer or vibration sensor 24 is detected. Sensor 24 and all the other sensors and electronic components were checked at decision points 114 and should be available to the idle loop. The idle loop at branch "B" preferably runs after the AI has reached injection temperature and preferably continues to run while the eAdaptor 10 is ON. The stand-alone loop is designed to sense when the eAdaptor and AI are left unattended. This stand-alone idle loop turns off the digital display screen 16 after a first predetermined idle or rest time to save battery power, and turns off eAdaptor 10 after a second predetermined idle or rest time. Preferably, the second predetermined idle time is longer than the first predetermined idle or rest time.

Referring back to FIG. 17b, this stand-along idle loop starts at "B" may optionally accessing/confirming the vibration sensor 24 at step 213, and determines whether the eAdaptor is active at decision point 214 using this sensor 24. The vibration sensor 24, which is preferably an accelerometer, can sense whether the eAdaptor is at rest or is being handled by the patients or HCPs. The accelerometer's readings would be substantially zero when the eAdaptor is idle. If the answer is "no," i.e., the eAdaptor is active, then the timeout counter is reset at step 216 and logic 100 runs a repeat loop until the eAdaptor and AI are idle. If the eAdaptor is idle at decision point 214, then logic 100 determines whether the idle time has exceeded the first predetermined idle time, e.g., 5 minutes, 10 minutes, etc. at decision point 218. If the first predetermined idle time is not reached, then logic 100 runs another repeat loop until the first predetermined idle time is reached. When reached, logic 100 turns digital display 16 off at step 220 to save power; however, the other sensors, processes and logic 100 in eAdaptor 10 remain active and continue to run.

Figure 17B:
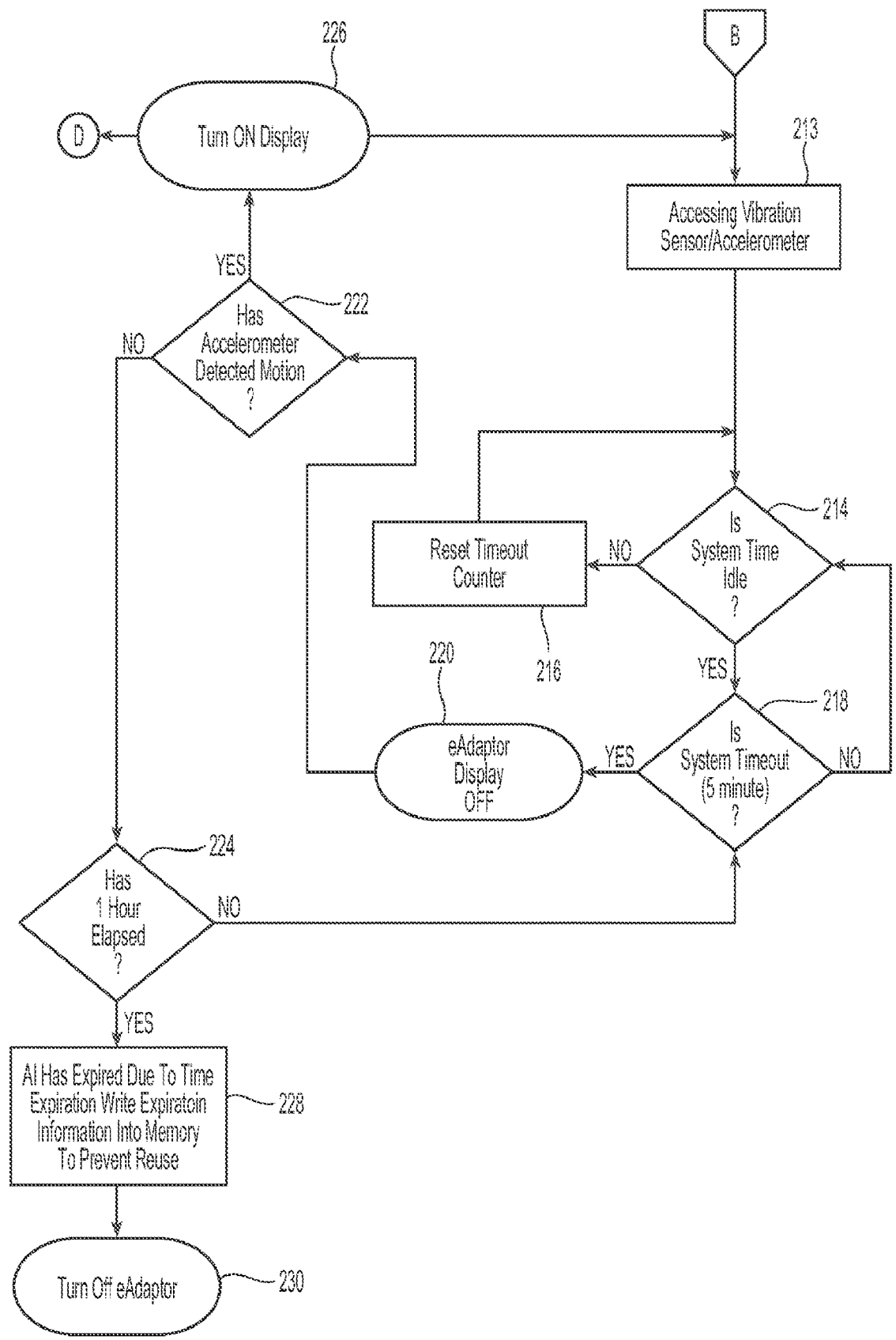
FIG. 17b shows a flow chart of an idle loop as branch "B" of the internal logic of FIG. 16

After digital display 16 is off, logic 100 determines at decision point 222 whether the accelerometer detects motion. If the accelerometer does not detect motion, the idle loop of logic 100 determines if the second predetermined idle time, e.g., 30 minutes, 1 hour or 2 hours, is reached at decision point 224. If the second predetermined time is not reached, then the idle loop returns to decision point 218 and runs a repeat loop to wait for either the second predetermined idle time expires at decision point 224 or the accelerometer detected motions at decision point 222. If motion is detected at decision point 222, which can be interpreted as the patients picked up the eAdaptor and AI, then logic 100 turns the digital display ON at step 226, and logic 100 would return to the start of branch "B" in FIG. 16, or optionally at any point upstream thereof. Preferably, the idle loop keeps running by returning to the start of branch "B" after step 226, as shown in FIG. 17b, to sense whether the eAdaptor and AI return to idle status.

The second predetermined idle time represents a time period after the AI was removed from refrigeration, when the medication contained in the AI is no longer safe to be injected into the patients. Hence, when the Boolean answer is "yes" at decision point 224, logic 100 would write the AI information from this particular AI into memory and would reject said AI at step 108 and decision point 109, discussed above, if the patients try to re-use this AI. Preferably, the second predetermined idle time is cumulative from the time the AI is inserted into the eAdaptor, so that if there are several idle time periods, logic 100 counts the total time since the AI was removed from refrigeration.

If the accelerometer is present and detected at decision point 222, the accelerometer can be used to wake up or turn digital screen 16 ON at step 226 by detecting vibrations/movements from the eAdaptor. Screen 16 would display whatever message(s) that was previously present before the screen was turn off. Since the system is active, logic 100 would then reset the timeout counter in step 216 and this stand-alone idle loop restarts.

As discussed above, the inventive eAdaptor 10 and internal logic 100 can distinguish among several failure modes, such as incomplete injection/dosing, premature removal of AI from the injection site, AI malfunction, expiration of AI, etc. The information can be stored, sent or made available to HCPs or doctors. Additionally, the APP on the smart phone can send reports of the improper or incomplete use to the HCPs or doctors, so that a replacement AI or a prescription for one can be sent to the patients.

Figure 18:
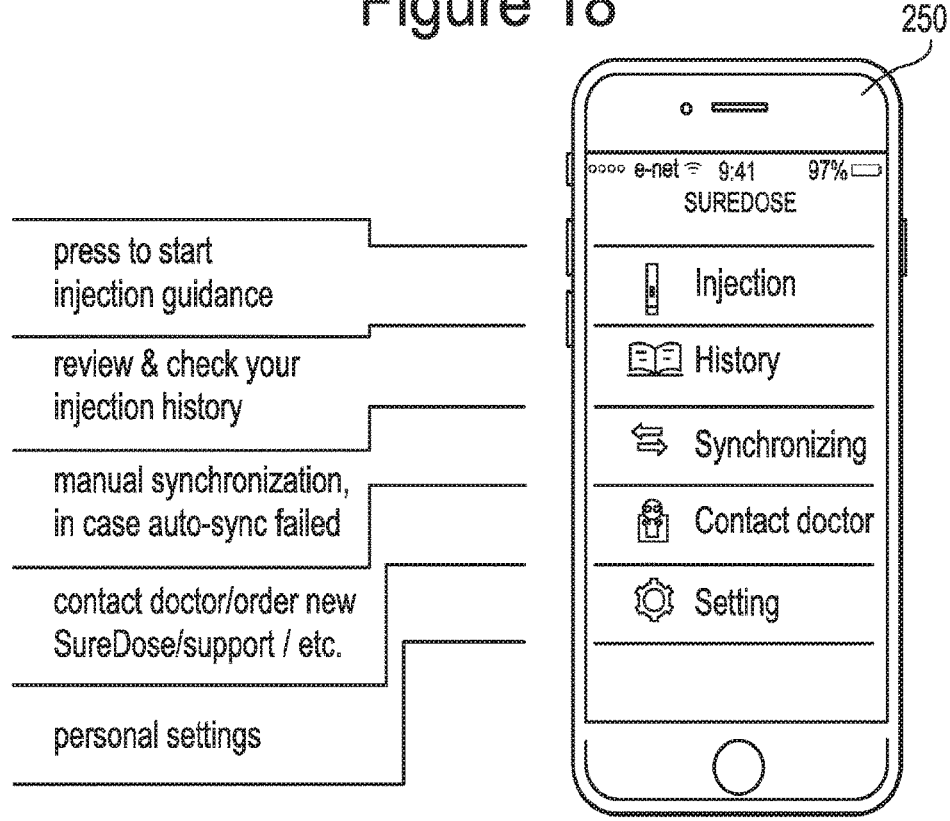
FIG. 18 is a graphical user interface (GUI) that show the home screen of a APP that resides in a smart device, such as a smart phone, that cooperates with the internal logic of the eAdaptor.
Figure 19:
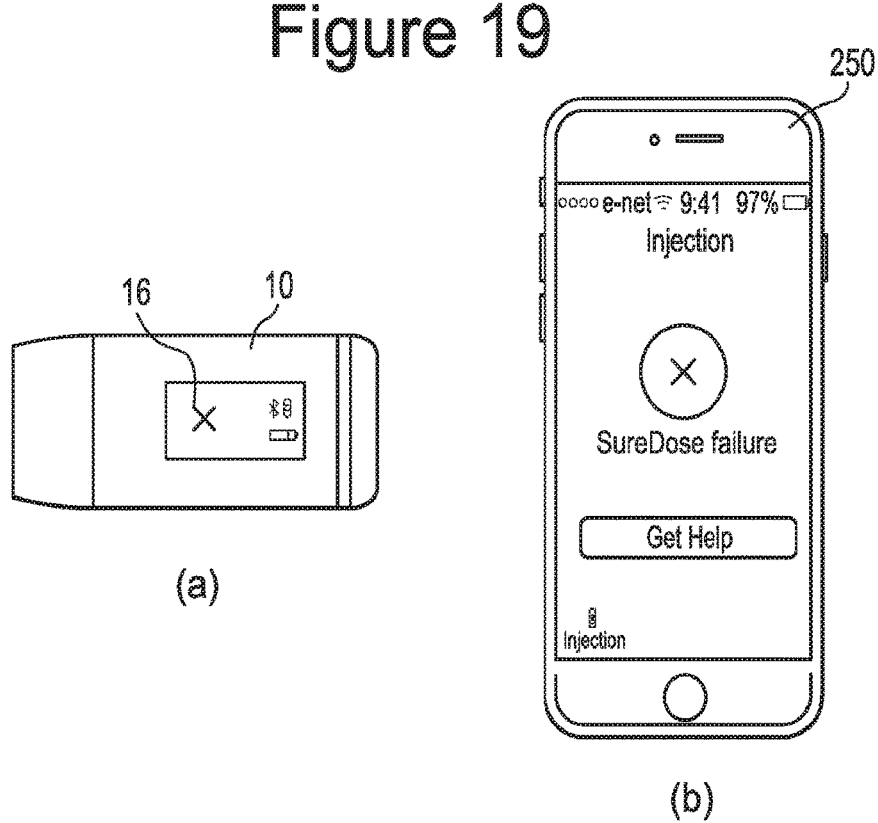
Figure 26:
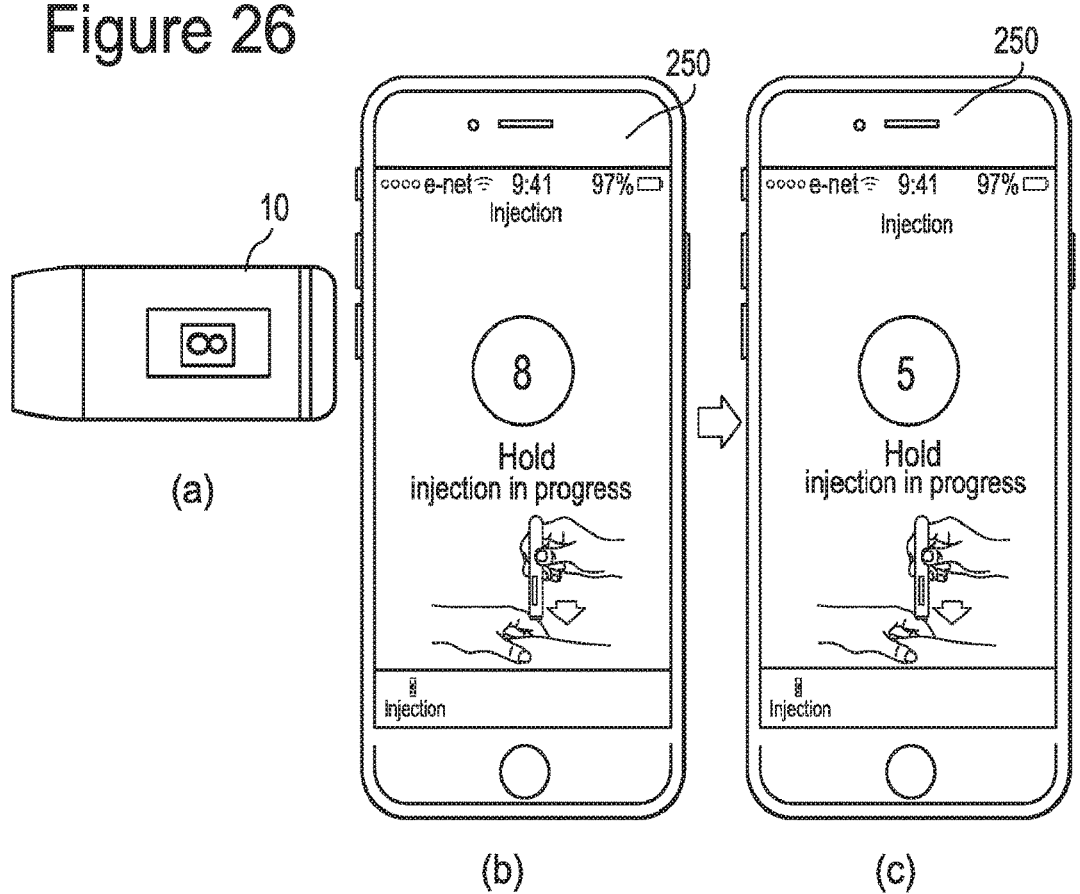
Figure 27:
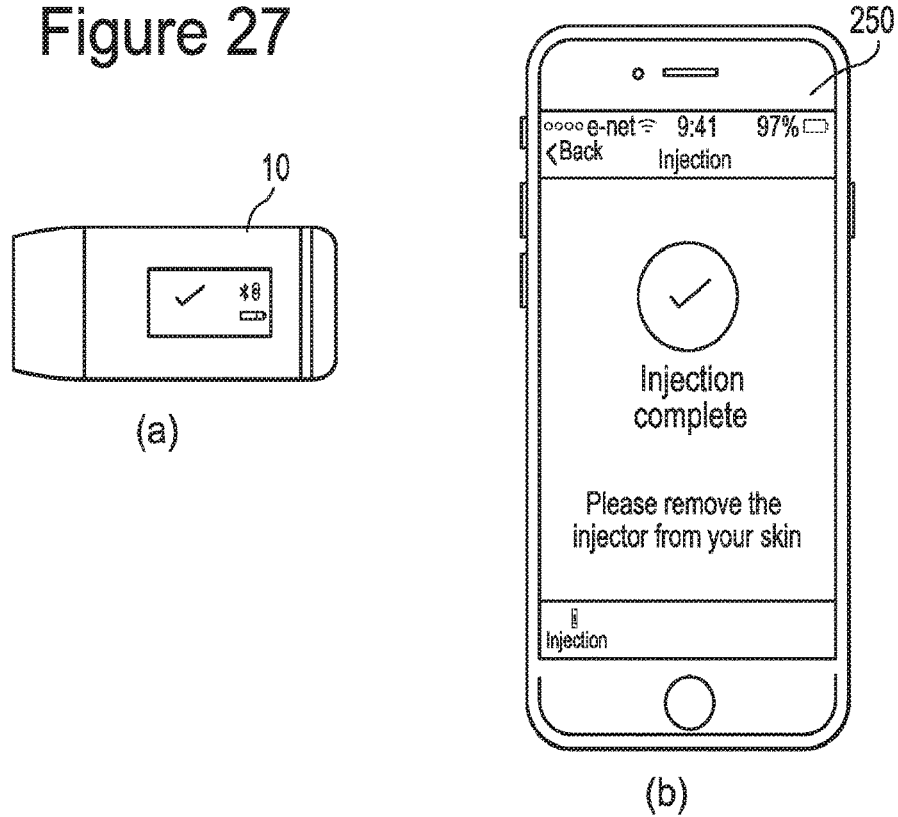

A graphical user interface (GUI) is designed to facilitate the patients' navigation of logic 100. Exemplary, non-limiting GUIs that may appear on the smart phone 250's screen and as well as on digital screen 16 of eAdaptor 10 are shown in FIGS. 18-32 and their subparts. A smartphone APP is connected to logic 100 after smart phone 250 is paired with eAdaptor 10. The smartphone APP displays messages to the users using the GUI. FIG. 18 shows an start screen, which gives the patients options for Injection, History, Synchronizing date and time between the phone and the eAdaptor, Contact Doctor or adjusting the Settings. By selecting one of these options, the patients can enter the APP on smart phone 250.

The display that the eAdaptor has failed discussed in step 126 of logic 110 is shown in FIGS. 19a-19b. Display 16 and smart phone 250 should have similar message with the smart phone showing additional texts due to its larger screen. FIGS. 20a-20b show the displays that the AI 30 is not properly attached to the eAdaptor 10 from step 138, and FIGS. 21a-21b show the displays that the AI is properly attached to the eAdaptor from step 140. FIGS. 22a-22b show the displays that there is no Bluetooth connection between the eAdaptor and the smart phone from step 134, and FIGS. 23a-23b show the displays that the eAdaptor and smartphone are connected via Bluetooth.

FIGS. 24a-24b show the display that the medication temperature has not yet reached the proper temperature, e.g., room temperature, from step 144, and FIGS. 25a-25b show the display that the medication temperature has reached the proper injection temperature from step 146. FIGS. 26a, 26b and 26c show the hold time and count down after the injection from step 166. FIGS. 27a-27b show the successful injection display from step 174, and FIGS. 28a-28b show the injection failure display from steps 158 and 164. FIGS. 29a-29b show the display that the used AI should be discarded from step 182. FIGS. 30a-30b show the number of uses/injections remaining for the eAdaptor from step 192, and FIGS. 31a-31b show the display that the eAdaptor should be discarded or recycled from step 190.

Preferably, the data calculation and manipulation are conducted on smart phone 250, since these smart devices would have a more robust processor and free up memory space on the eAdaptor. Although such calculation and manipulation can be conducted by microprocessor 58 on the eAdaptor. The data calculation and manipulation can produce results such as time of injection, time duration of injection, injection failure or success, etc. FIG. 32a show the GUI from FIG. 18 when the History option is selected. The injection history can be displayed in compact form with a listing of the past injection events as shown in FIG. 32b or with more details shown on one or more screen as shown in FIG. 32c.

III. Training and Simulation APP

To provide training for new users or patients, the potential eAdaptor failure and success modes are preferably presented by an APP to the users for the users to gain familiarity and expertise with the device. To create each possible failure modes on the actual eAdaptor would be costly and materially prohibitive. The present inventors have created a training or simulation APP for the new users.

Referring to FIGS. 33a-33c, the training APP comprises an administrator page. Within this administrator page, each of the potential eAdaptor failure points, such as injection temperature not reached, sensor error, etc., can be selected by choosing the "On" option. The "Off" option means that the error or failure would not occur. After selection and confirmation, the training APP will simulate eAdaptor 10 to behave as if each of the selected failures have occurred. Within the administrator page, a "Restore" or "Default" option is present to quickly restore the eAdaptor and APP to the normal state to detect errors or failures, as discussed above.

With training the patients or users would know how to use eAdaptor 10 under those conditions or scenarios. With such training, the patients would know what actions to take in the event that error(s) or failure(s) occurs.

Alternatively, the smart phone APP discussed above can take the error/failure data from actual injection(s) collected from eAdaptor 10 and populate the "On" or "Off" options shown on the administration page shown in FIGS. 33a and 33b. When the patients save these errors/failures shown in FIG. 33c, the APP instructs the patients the next course(s) of action, such as, the errors do not negate the validity of the injection but contact the doctors to report, repeat the injection with a new AI, contact the doctors for further instructions, etc.

IV. Human Factor/User Evaluation Study

A user evaluation study was performed. eAdaptors 10 were presented to 16 participants comprising 6 Asthma patients, 5 chronic obstructive pulmonary disease (COPD) patients, and 5 caregivers to COPD/Asthma patients. When presented with the option (i) to self-administer Autoinjector 30 with eAdaptor 10 and associated APP/logic 100, or (ii) to self-administer Autoinjector 30 by itself, 14 out of 16 participants (87.5%) chose to use eAdaptor 10 and associated APP/logic 100. Of the two who did not initially choose to use the eAdaptor and associated APP, after the study facilitator/administrator explained the purpose of the eAdaptor and associated APP, one participant, a COPD patient, stated that it would probably be better to use it. The other participant was a caregiver.

The participants also reported that the use of red and green indicator lights with green means everything is satisfactory and red means an error situation. This coloring scheme was tested during the user evaluation study and found to be user expected.

The participants also found that the shape of eAdaptor 10, as an add-on that covers from about ⅓ to ½ of Autoinjector 30's back end, improved the grip for the participants and provided easier injection. This was also confirmed by the user evaluation study.

The participants also described that displaying step-by-step guidance for the users to follow on the eAdaptor's display during injection step was helpful. This step-by-step guidance helped assure the participants or patients, especially new patients, that they are administering the drug correctly. This was also confirmed by the user evaluation study.

The participants also reported that the synchronization of eAdaptor 10's screen to the APP and the smartphone's screen would help patients. Some patients may want to use the eAdaptor screen while others may want to use the APP screen to guide their injection process. This value-added synchronization was also confirmed by the user evaluation study.

While it is apparent that the illustrative embodiments of the invention disclosed herein fulfill the objectives stated above, it is appreciated that numerous modifications and other embodiments may be devised by those skilled in the art. One such modification is that speaker 62 may broadcast verbal instructions similar to the displayed messages as GUIs on the smart device or on digital screen 16. Therefore, it will be understood that the appended claims are intended to cover all such modifications and embodiments, which would come within the spirit and scope of the present invention.

We claim:

1. An external adaptor adapted to receive an automatic injector (AI) therewithin and to sense at least one characteristic of an injection by the AI at an injection site comprising:

a sound sensor to detect a first sound produced by the AI at a start of the injection and a second sound produced by the AI at an end of the injection, a vibration sensor to detect a first movement produced by the AI at the start of the injection and a second movement produced by the AI at the end of the injection, and a real time clock (RTC) connected to a microprocessor to provide a timeline for the sensors, wherein the microprocessor determines a start time for the injection when the first sound detected by the sound sensor and the first movement detected by the vibration sensor substantially coincide on the time line and wherein the microprocessor determines an end time for the injection when the second sound detected by the sound sensor and the second movement detected by the vibration sensor substantially coincide on the time line.

2. The external adaptor of claim 1 further comprising at least one magnetic sensor adapted to sense at least one magnetic member in the AI, wherein said at least one magnetic member is attached to a movable member in the AI and said movable member is moved from an initial location to a start location to start the injection, wherein at the initial location the at least one magnetic sensor senses a first magnetic reading, wherein at the start location the at least one magnetic member is proximate to the at least one magnetic sensor and the at least one magnetic sensor senses a second magnetic reading, which is higher than the first magnetic reading, and wherein the microprocessor determines a magnetic start time at the start location.

3. The external adaptor of claim 2, wherein after the end of the injection the AI is removed from the injection site, the movable member returns at least to its initial location and the at least one magnetic sensor senses a third magnetic reading, which is less than or equal to the first magnetic reading, and wherein the microprocessor determines a magnetic removal time when the at least one magnetic sensor senses the third magnetic reading.

4. The external adaptor of claim 1, wherein an injection duration is a difference between the start time and the end time.

5. The external adaptor of claim 4, wherein a total time at the injection site is a difference between the magnetic start time and the magnetic removal time.

6. The external adaptor of claim 5, wherein a hold time at the injection site is the total time at injection site less the injection duration.

7. The external adaptor of claim 1 further comprising a temperature sensor.

8. The external adaptor of claim 7, wherein the temperature sensor is an infrared temperature sensor or a thermistor.

9. The external adaptor of claim 2 further comprising at least one spring to bias the AI.

10. The external adaptor of claim 1 further comprising at least one of a digital screen, at least one LED light and at least one speaker.

11. The external adaptor of claim 1, wherein the vibration sensor comprises an accelerometer.

12. The external adaptor of claim 2 further comprising a near field communication (NFC) reader, which is adapted to read an information on a NFC tag located on the AI.

13. A combination of an external adaptor and an automatic injector (AI), wherein the AI is received at least partially within the external adaptor, wherein the combination comprises at least one magnetic sensor disposed within the external adaptor and is adapted to sense at least one magnetic member in the AI, wherein said at least one magnetic member is attached to a movable member in the AI and said movable member is moved from an initial location to a start location to start an injection of the AI at an injection site, wherein at the initial location the at least one magnetic sensor senses a first magnetic reading, wherein at the start location the at least one magnetic member is proximate to the at least one magnetic sensor and the at least one magnetic sensor senses a second magnetic reading, which is higher than the first magnetic reading, and wherein a microprocessor using a real time clock (RTC) determines a magnetic start time at the start location.

14. The combination of claim 13, wherein after the end of the injection the AI is removed from the injection site, the movable member returns at least to its initial location and the at least one magnetic sensor senses a third magnetic reading, which is less than or equal to the first magnetic reading, and wherein the microprocessor determines a magnetic removal time when the at least one magnetic sensor senses the third magnetic reading.

15. The combination of claim 13, wherein the external adaptor further comprises
    a sound sensor to detect a first sound produced by the AI at a start of the injection and a second sound produced by the AI at an end of the injection,
    a vibration sensor to detect a first movement produced by the AI at the start of the injection and a second movement produced by the AI at the end of the injection, and
    wherein the microprocessor determines a start time for the injection when the first sound detected by the sound sensor and the first movement detected by the vibration sensor substantially coincide on the time line and wherein the microprocessor determines an end time for the injection when the second sound detected by the sound sensor and the second movement detected by the vibration sensor substantially coincide on the time line.

16. The combination of claim 15, wherein an injection duration is a difference between the start time and the end time.

17. The combination of claim 16, wherein a total time at the injection site is a difference between the magnetic start time and the magnetic removal time.

18. The combination of claim 17, wherein a hold time at the injection site is the total time at injection site less the injection duration.

19. The combination of claim 13, wherein the external adaptor and the AI have substantially cylindrical shape and the AI is inserted into the external adaptor at any orientation.

20. The combination of claim 19, wherein the at least one magnetic sensor comprises a predetermined effective sensing angular arc and a number of the at least one magnetic sensor and a number of the at least one magnetic member are determined based on said predetermined effective sensing angular arc.

21. The combination of claim 13, wherein the at least one magnetic sensor comprises a plurality of magnetic sensors that are positioned to sense an angular arc of about 90°, and the at least one magnetic member comprises a plurality of magnetic members that are positioned about 90° apart.

22. The combination of claim 13 further comprising at least one spring to bias the AI toward the external adaptor.

23. The combination of claim 13 further comprising a temperature sensor.

24. The combination of claim 23, wherein the temperature sensor is an infrared temperature sensor or a thermistor.

25. The combination of claim 13 further comprising at least one of a digital screen, at least one LED light and at least one speaker.

26. The combination of claim 15, wherein the vibration sensor comprises an accelerometer.

27. The combination of claim 13 further comprising a near field communication (NFC) reader located on the external adaptor, which is adapted to read an information on a NFC tag located on the AI.

28. The combination of claim 13 further comprising a reader located on the external adaptor, which is adapted to read an information on an identification code located on the AI.

29. The combination of claim 28, wherein the identification code comprises a bar code or a matrix bar code.

30. The combination of claim 28, wherein the identification code is connected to an external source of information for the AI.

* * * * *